(12) United States Patent
Becher et al.

(10) Patent No.: US 11,951,157 B2
(45) Date of Patent: Apr. 9, 2024

(54) METHODS OF TREATING MALIGNANT TUMOUR WITH IL-12 AND ANTI-PD-1 ANTIBODY

(71) Applicant: UNIVERSITAT ZURICH, Zurich (CH)

(72) Inventors: Burkhard Becher, Maur (CH); Johannes Vom Berg, Zurich (CH)

(73) Assignee: UNIVERSITAT ZURICH, Zurich (CH)

( * ) Notice: Subject to any disclaimer, the term of this patent is extended or adjusted under 35 U.S.C. 154(b) by 0 days.

(21) Appl. No.: 16/357,756

(22) Filed: Mar. 19, 2019

(65) Prior Publication Data

US 2019/0201493 A1 Jul. 4, 2019

Related U.S. Application Data

(63) Continuation-in-part of application No. 14/350,362, filed as application No. PCT/EP2012/070088 on Oct. 10, 2012, now abandoned.

(60) Provisional application No. 61/573,200, filed on Sep. 26, 2011.

(30) Foreign Application Priority Data

Oct. 11, 2011 (EP) .................................... 11184644
Nov. 10, 2011 (EP) .................................... 11188625
Sep. 19, 2012 (EP) .................................... 12185108

(51) Int. Cl.
| | | |
|---|---|---|
| A61K 38/20 | (2006.01) | |
| A61K 9/00 | (2006.01) | |
| A61K 39/395 | (2006.01) | |
| A61P 35/00 | (2006.01) | |
| C07K 14/54 | (2006.01) | |
| C07K 16/28 | (2006.01) | |
| A61K 39/00 | (2006.01) | |

(52) U.S. Cl.
CPC .......... *A61K 38/208* (2013.01); *A61K 9/0019* (2013.01); *A61K 9/0085* (2013.01); *A61K 39/39516* (2013.01); *A61K 39/3955* (2013.01); *A61P 35/00* (2018.01); *C07K 14/5434* (2013.01); *C07K 16/2818* (2013.01); *A61K 2039/505* (2013.01); *A61K 2039/545* (2013.01); *C07K 2317/21* (2013.01); *C07K 2319/30* (2013.01)

(58) Field of Classification Search
CPC ............... A61K 38/208; A61K 9/0019; C07K 14/5434; C07K 2319/30; A61P 35/00
See application file for complete search history.

(56) References Cited

U.S. PATENT DOCUMENTS

| | | | |
|---|---|---|---|
| 5,116,964 A | 5/1992 | Capon et al. | |
| 5,573,764 A | 11/1996 | Sykes et al. | |
| 5,994,104 A | 11/1999 | Anderson et al. | |
| 8,008,449 B2 | 8/2011 | Korman et al. | |
| 8,067,227 B2 | 11/2011 | Waehler | |
| 2002/0193570 A1 | 12/2002 | Gillies et al. | |
| 2003/0011856 A1 | 1/2003 | Kasahara et al. | |
| 2009/0028857 A1 | 1/2009 | Li et al. | |
| 2010/0330046 A1* | 12/2010 | Comer ................. A61K 38/208 424/93.7 |

FOREIGN PATENT DOCUMENTS

| | | |
|---|---|---|
| AU | 2008311292 | 4/2009 |
| EP | 1537878 | 6/2005 |
| JP | 2020-200346 | 12/2020 |
| WO | 1997/020574 | 6/1997 |
| WO | 00/75292 | 12/2000 |
| WO | 2006/121168 | 11/2006 |
| WO | 2009/014708 | 1/2009 |
| WO | 2010/042189 | 4/2010 |
| WO | 2011/119773 | 9/2011 |
| WO | 2011/161699 | 12/2011 |

OTHER PUBLICATIONS

Clinical Trial NCT01295827 (Feb. 15, 2011).*
Scheerlinck, J.P. Functional and structural comparison of cytokines in different species. Vet Immunol Immunopathol. Dec. 15, 1999; 72(1-2):39-44.*
Zhen et al "Multiple extracranial metastases from secondary glioblastoma multiforme: a case report and review of the literature", J. Neurooncology, 97:451-457, 2010.
P. L. Triozzi: "Phase I Study of the Intratumoral Administration of Recombinant Canarypox Viruses Expressing B7.1 and Interleukin 12 in Patients with Metastatic Melanoma". Clinical Cancer Research, vol. 11, No. 11, Jun. 1, 2005 , pp. 4168-4175.
Sabel et al: "Synergistic effect of intratumoral IL-12 and TNF-alpha microspheres: systemic anti-tumor immunity is mediated by both CD8+ CTL and NK cells", Surgery, Nov. 2, 2007 pp. 749-760.
Zhong Rui-Kun et al: "Induction, selection and expansion of acute myeloid leukemia reactive autologous T cells for adoptive immunotherapy", Blood; , vol. 106, No. 11 part 1, Nov. 16, 2005, pp. 1-2.

(Continued)

*Primary Examiner* — Dong Jiang
(74) *Attorney, Agent, or Firm* — JMB Davis Ben-David

(57) ABSTRACT

The invention relates to a combination medicament for treatment of malignant neoplastic disease. The combination medicament comprises an IL-12 polypeptide having a biological activity of IL-12 or a nucleic acid expression vector comprising a sequence encoding such IL-12 polypeptide, and a non-agonist blockade of T-cell inhibitory molecules, including non-agonist LAG-3 ligand, non-agonist TIM-3 ligand, non-agonist BLTA ligand, non-agonist TIGIT ligand, non-agonist VISTA ligand, non-agonist B7/H3 ligand, non-agonist CTLA-4 ligand or non-agonist PD-1 ligand, particularly an anti-CTLA-4 or anti-PD-1 immunoglobulin G.

9 Claims, 9 Drawing Sheets

Specification includes a Sequence Listing.

(56) References Cited

OTHER PUBLICATIONS

P. E. Fecci Ei Al: "Systemic CTLA-4 Blockade Ameliorates Glioma-Induced Changes to the CD4+ T Cell Compartment without Affecting Regulatory T-Cell Function", Clinical Cancer Research, vol. 13, No. 7, Apr. 1, 2007, pp. 2158-2167.
Yunhui Liu et al: "In situ adenoviral interleukin 12 gene transfer confers potent and long-lasting cytotoxic immunity in glioma", Cancer Gene Therapy, vol. 9, No. 1, Jan. 1, 2002, pp. 9-15.
O'Day et al. "Efficacy and safety of ipilmumab monotherapy in patients with pretreated advanced melanoma: a multicenter single-arm phase II study." Ann Oncol. Aug. 21, 2010(8):1712-1717 Epub Feb. 10, 2010.
Eisenring et al. "IL-12 initiates tumor rejection via lymphoid tissue-inducer cells bearing the natural cytotoxicity receptor NKp46" Nat Immunol, Nov. 11, 2010(11), 1030-1038, Epub Oct. 10, 2010.
Zaharoff et al. "Intratumoral immunotherapy of established solid tumors with chitosan /IL-12" J Immunother. Sep. 2010 33(7) 697-705.
Simmons et al. "Local secretion of anti-CTLA-4 enhances the therapeutic efficacy of a cancer immunotherapy with reduced evidence of systemic autoimmunity" Cancer Immunol Immunother, Aug. 2008, 57(8) 1263-1270, Epub Jan. 31, 2008.
Malvicini et al, "Reversal of gastrointestinal carcinoma-induced immunosuppression and induction of antitumoral immunity by a combination of cyclophosphamide and gene transfer of IL-12" Molecular Oncology, Jun. 2011, vol. 5, No. 3, p. 242-255.
Kaneda, "Therapeutic strategies for controlling metastasis and recurrance of cancers," Drug Delivery System, 2010, vol. 25, No. 2, p. 94-102.
Onishi et al. "New immunotherapy against cancer: A therapy to control regulatory T Cell" Fukuoka Igaku Zasshi (Fukuoka Medical Journal), 2010, vol. 101, No. 10, p. 207-214 (Figures in English).
Curran et al. "PD-1 and CTLA-4 combination blockade expands infiltrating T cells and reduces regulatory T and myeloid cells within B16 melanoma tumors," Proc. Natl. Acad. Sci. USA, 2010, vol. 107, No. 9, p. 4275-4280.
Quetglas et al., "Virotherapy with a Semliki Forest Virus-Based Vector Encoding IL 12 Synergizes with PD-1/PD-L1 Blockade," Cancer Imm. Res. 3:449-454, 2015.
Quetglas et al., "Immunotherapeutic Synergy Between Anti-CD137 mAb and Intratumoral Administration of a Cytopathic Semliki Forest Virus Encoding IL-12" Molecular Therapy, Jun. 2012, 20(9), pp. 1664-1675.
Seliger and Quandt, 2012, The expression, function, and clinical relevance of the B7 family members in cancer, Cancer Immunol. Immunother. 61 :1327-1341.
Haile et al., 2011, Tumor Cell Programmed Oeath Ligand 1-Mediated T Cell Suppression is Overcome by Coexpression of CD80, Journal of Immunology 186:6822-6829.
Ascierto et al., "Clinical experiences with anti-CD137 and anti-PD1 therapeutic antibodies" Seminars in Oncology, 2010,37(5), pp. 508-516.
Flemming, "PD-1 makes waves in anticancer immunotherapy" Nature Reviews Drug Discovery, Aug. 2012, 11 (8), p. 601.
Topalian et al., "Safety, Activity, and Immune Correlates of Anti-PD-1 Antibody in Cancer" N. Engl. J. Med., Jun. 2012, 366(26), pp. 2443-2454.
Brahmer et al., "Safety and Activity of Anti-PD-L1 Antibody in Patients with Advanced Cancer" N. Engl. J. Med., Jun. 2012, 366(26), pp. 2455-2465.
Dei Vecchio et al., "Interleukin-12: biological properties and clinical application " Clin. Cancer Res., 2007, 13(16), pp. 4677-4685.
Mangsbo et al., "Enhanced tumor eradication by combining CTLA-4 or PD-1 blockade with CpG therapy " J. Immunother., 2010,33(3), pp. 225-235.
Wong et al., 2007, Programmed death-1 blockade enhances expansion and functional capacity of human melanoma antigen-specific CTLs, International Immunology 19:1223-1234.
Topalian et al., 2012, Targeting the PD-1/B7-H1 (PD-L 1) pathway to activate anti-tumor immunity, Current Opinion in Immunology 24:207-212.
Simeone and Ascierto, 2012, Immunomodulating antibodies in the treatment of metastatic melanoma: The experience with anti-CTLA-4, anti-CD137, and anti-PD1, Journal of Immunotoxicology, 9:241-247.
Berenbaum (1977) "Synergy, additivism and antagonism in immunosuppression" Clinical ExperimentalImmunology 28:1-18.
Weber (2010) "Immune Checkpoint Proteins: A New Therapeutic Paradigm for Cancer—Preclinical Background: CTLA-4 and PD-1 Blockade" Seminars on Oncology 37(5): 430-439.
Shirabe et al. (2010) "Tumor-infiltrating lymphocytes and hepatocellular carcinoma: pathology and clinical management" International Journal of Clinical Oncology 15: 552-558.
Zabala et al. (2007) "Induction of immunosuppressive molecules and regulatory T cells counteract the antitumor effect of interleukin-12-based gene therapy in a transgenic mouse model of liver cancer" Journal of Hepatology 47: 807-815.
Rudnick et al. (2009) "Affinity and avidity in antibody-based tumor targeting" Cancer Biotherapy and Radiopharmaceuticals 24(2): 155-161.
Beckman et al. (2006) "Antibody constructs in cancer therapy" Cancer 1 09(2): 170-179.
Mahvi et al. (2007) "Intratumoral injection of IL-12 plasmid DNA-results of a phase I/IB clinical trial" Cancer Gene Therapy 14: 717-723.
Rakhmilevich et al. (1997) "Cytokine gene therapy of cancer using gene gun technology: superior antitumor activity of Interleukin-12" Human Gene Therapy8: 1303-1311.
Watanabe et al. (1999) "Intradermal delivery of IL-12 naked DNA induces systemic NK cell activation and Th1 response in vivo that is independent of endogenous IL-12 production" The Journal of Immunology 163: 1943-1950.
Saffran et al. (1998) "Immunotherapy of established tumors in mice by intratumoral injection of interleukin-2 plasmid DNA: Induction of CD8+ Tcell immunity" Cancer Gene Therapy 5: 321-330.
Colombo et al. (1996) "Amount of interleukin 12 available at the tumor site is critical for tumor regression" Cancer Reasearch 56: 2531-2534.
Rakhmilevich et al. (1999) "Gene gun-mediated IL-12 gene therapy induces antitumor effects in the absence of toxicity: a direct comparison with systemic IL-12 protein therapy" Journal of Immunotherapy 22: 135-144.
Weber et al. (1998) "Interleukin-12 gene transfer results in C08-dependent regression of murine CT26 liver tumors" Annals of Surgical Oncology 6: 186-194.
Oshikawa et al. (1999) "Synergistic inhibition of tumor growth in a murine mammary adenocarcinoma model by combinational gene therapy using IL-12, pro-IL-18, and IL-1 ß converting enzyme cDNA" Proceedings of the National Academy of the Sciences of the United States of America 96(23): 13351-13356.
Takahara et al. (1995) "Effective eradication of established murine tumors with IL-12 gene therapy using a polycistronic retroviral vector" The Journal of Immunology 154: 6466-6474.
Zitvogel et al. (1995) "Cancer immunotherapy of established tumors with IL-12. Effective delivery by genetically engineered fibroblasts." The Journal of Immunology 155: 1393-1403.
Pardoll et al. (2012) "The blockade of immune checkpoints in cancer immunotherapy" Nature Reviews Cancer 12: 252-264.
Liu et al. (2019) "Study of the interactions of a novel monoclonal antibody, mAb059c, with the hPD-1 receptor" Scientific Reports 9: 17830.
Markham et al. (2018) "Cemiplimab: first global approval" Drugs 78: 1841-1846.
Kumar et al. (2021) "Preclinical characterization of dostarlimab, a therapeutic anti-PD-1 antibody with potent activity to enhance immune function in in vitro cellular assays and in vive animal models" mAbs 13(1): 1-12.
Aydin et al. (2017) "Spotlight on atezolizumab and its potential in the treatment of advanced urothelial bladder cancer" OncoTargets and Therapy10: 1478-1502.

(56) References Cited

OTHER PUBLICATIONS

Liu et al. (2017) "Structural basis of anti-PD-L 1 monoclonal antibody avelumab for tumor therapy" Cell Research 27: 151-153.
Picardo et al. (2019) "Structure and optimization of checkpoint inhibitors" Cancers 12(38): 1-15.
Perez-Gracia et al. (2009) "Clinical development of combination strategies in immunotherapy: are we ready for more than on investigational product in an early clinical trial?" Immunotherapy 1 (5): 845-853.
Yu et al. (2010) "Simultaneous blockade of multiple immune system inhibitory checkpoints enhances antitumour activity mediated by interleukin-15 in a murine metastatic colon carcinoma model" Cancer Therapy: Preclinical 16(24): 6019-6028.
Shimizu et al. (2002) "Stimulation of CD25+CD4+ regulatory T cells through GITR breaks immunological self-tolerance" Nature Immunology 3(2): 135-142.
Carson et al. (2010) "Braking bad: blockade of inhibitory pathways improves interleukin-15 therapy" Clinical Cancer Research 16(24): 5917-5919.
Li et al. (2009) "Anti-Programmed Death-1 Synergizes with Granulocyte Macrophage Colony-Stimulating Factor-Secreting Tumor Cell Immunotherapy Providing Therapeutic Benefit to Mice with Established Tumors" Clin Cancer Res 15(5): 1623-1634.
Selby et al. (2016) "Preclinical Development of Ipilimumab and Nivolumab Combination Immunotherapy: Mouse Tumor Models, In Vitro Functional Studies, and Cynomolgus Macaque Toxicology" PLOS One 11 (9):1-19.
Chen (2004) "Co-inhibitory molecules of the B7-CD28 family in the control of T-cell immunity" Nature Reviews Immunology 4:336-347.
Xu et al., (2010) "Regulation of antitumor immune responses by the IL-12 family cytokines, IL-12, IL-23, and IL-27" Clinical and Developmental Immunology 832454:1-9.
Vanneman & Oranoff (2012) "Combining immunotherapy and targeted therapies in cancer treatment" Nature Reviews Cancer 12:237-251.
Bramson et al. (1996) "Direct Intratumoral Injection of an Adenovirus Expressing Interleukin-12 Induces Regression and Long-Lasting Immunity That Is Associated with Highly Localized Expression of Interleukin-12" Human Gene Therapy 7:1995-2002.
Egilmez et al. (2007) "Controlled-release Particulate Cytokine Adjuvants for Cancer Therapy" Endocrine, Metabolie & Immune Oisorders—Orug Targets 7:266-270.
Choi et al. (2012) "Strengthening of antitumor immune memory and prevention of thymic atrophy mediated by adenovirus expressing IL-12 and GM-CSF" Gene Therapy 19:711-723.
Egilmez and Kilinc, 2010, Tumor-Resident C08+ T-cell: The Critical Catalyst in IL-12-Mediated Reversal of Tumor Immune Suppression, Arch. Immunol. Ther. Exp. 58:399-405.
Schmidt (2009) "Fusion proteins as biopharmaceuticals—applications and challenges" Current Opinion in Drug Discovery & Oevelopment 12(2):1-12.
InvivoGen review: Immunoglobulin G (2011), available at https://www.invivogen.com/review-antibody-generation (1 page).
Huang et al. (2015) "The PD-1/B7-H1 Pathway Modulates the Natural Killer Cells versus Mouse Glioma Stem Cells" PLoS ONE 10(8):e0134715.
Patnaik et al., Phase I study of MK-3475 (anti-PD-1 monoclonal antibody) in patients with advanced solid tumors, J Clinical Onc. 30(15) May 20, 2012.
Vom Berg, Interleukin-12 in combination with CTLA-4 blockade leads to T-cell dependent rejection of advanced stage glioma, 2012 058a Extract fram ResearchGate showing publication of 04 (Vom Berg PhD) by Jan. 2012 (avaialable online at zora.uzh.ch).

Turnis and Rooney, Enhancement of dendritic cells as vaccines for cancer, 2010, Immunotherapy 2(6) 847-862.
Chikkanna-Gowda et al., Regression of mouse tumours and inhibition of metastases following administration of a Semliki Forest virus vector with enhanced expression of IL-12, 2005, Gene Therapy 12:1253-1263.
Pützer et al., Interleukin 12 and B7-1 costimulatory molecule expressed by an adenovirus vector act synergistically to facilitate tumor regression, 1997, PNAS 94:10889-10894.
Corzo, Time, the forgotten dimension of ligand binding teaching, 2006, Biochem. and Mol Biol. Edu. 34:413-416.
Pavlin et al., 2009, Local and systemic antitumor effect of intratumoral and peritumoral IL-12 electragene therapy on murine sarcoma, Cancer Biology & Therapy 8:2112-2120.
Cheng et al., 2007, The PD-1/PD-L pathway is up-regulated during IL-12-induced suppression of EAE mediated by IFN-gamma, Journal of Neuroimmunology 185:75-86.
Malvicini et al "Reversal of gastrointestinal carcinoma-induced immunosuppression and induction of antitumoural immunity by a combination of cyclophosphamide and gene transfer of IL-12," Molecular Onc. 5:242-255, 2012.
Kaneda, "Therapeutic strategies for controlling metastasis and recurrance of cancers," Drug Delivery System 25:94-102, 2010.
Barone et al. "Effect of in vivo administration of anti-CTLA-4 monoclonal antibody and IL-12 on the induction of low-dose oral tolerance", Clinical and Experimental Immunology, 2002, vol. 130, pp. 196-203.
Liu et al. "Therapeutic efficacy and cellular 1-13 mechanism Nediated by intratumoral and intramuscular IL-12 electrogenetherapy", Molecular Therapy, Academic Press, San Diego, CA, US, vol. 9, May 1, 2004 (May 1, 2004), p. 222.
Curran et al "PD-1 and CTLA-4 combination blockade expands infiltrating T cells and reduces regulatory T and myeloid cells within B16 melanoma tumors," Proc Natl Acad Sci, Mar. 2, 2010;107(9):4275-80.
Rich et al., "A Practical Guide To Understanding Kaplan-Meier Curves," Otolaryngol Head Neck Surg, 143:331-336, 2010.
Szatmari et al.: "Detailed characterization of the mouse glioma 261 tumor model for experimental glioblastoma therapy", Cancer Sci, vol. 97, No. 6, 546-553.
Vetter et al.: "Intracerebral Interleukin 12 Induces Glioma Rejection in the Brain Predominantly by CD8+ T Cells and Independently of Interferon—y", Neuropathol Exp Neural, vol. 68, No. 5, 2009.
Glaesner et al.: "Engineering and characterization of the long-acting glucagonlike peptide-l analogue LY218926S, an Fc fusion protein", Diabetes Metab Res Rev 2010, 26, 287-296.
Grauer et al.: "CD4+ FoxP3+ regulatory T ccHs gradually accumulate iu gliomas during tumor growth and efficiently suppress antigliom'l immune responses in vivo", Int. J. Cancer: 121, 95-105 (2007).
Ascierto et al "Clinical experiences with anti-CD137 and anti-PD1 therapeutic antibodies", Seminars In Onco, Elsevier, US, vol. 37, No. 5, Oct. 1, 2010, pp. 508-516._XP8175440A Dont Have Copy.
Mangsbo et al "Enhanced Tumor Eradication by Combining CTLA-4 or PD-1 Blockade With CpG Therapy", Journal of Immunotherapy, Lippincott Williams & Wilkins, US, vol. 33, No. 3, Apr. 1, 2010, pp. 225-235, ISSN: 1524-9557_XP009144370 Dont Have Copy.
Hellums et al. "Increased efficacy of an interleukin-12-secreting herpes simplex virus in a syngeneic intracranial murine glioma model", Neuro-Oncology, 2005, vol. 7, No. 3, p. 213-224.
Jacobs et al. "Regulatory T cells and the PD-L 1/PD-1 pathway mediate immune suppression in malignant human brain tumors" Neuro-Oncology, 2009, vol. 11, No. 4, p. 394-402, doi:10.1215/15228517-2008-104.

\* cited by examiner

PBS/PBS vs IL-12Fc/αPD-1 P = 0.0064

SEQUENCE LISTING

```
<160> NUMBER OF SEQ ID NOS: 9

<210> SEQ ID NO 1
<211> LENGTH: 775
<212> TYPE: PRT
<213> ORGANISM: artificial
<220> FEATURE:
<223> OTHER INFORMATION: fusion between human IL-12 and IgG4 Fc

<400> SEQUENCE: 1

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
```

-continued

```
            115                 120                 125
Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
        210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
        290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Ser Gly Gly Gly
                325                 330                 335

Gly Ser Gly Gly Gly Gly Ser Arg Asn Leu Pro Val Ala Thr Pro Asp
            340                 345                 350

Pro Gly Met Phe Pro Cys Leu His His Ser Gln Asn Leu Leu Arg Ala
        355                 360                 365

Val Ser Asn Met Leu Gln Lys Ala Arg Gln Thr Leu Glu Phe Tyr Pro
        370                 375                 380

Cys Thr Ser Glu Glu Ile Asp His Glu Asp Ile Thr Lys Asp Lys Thr
385                 390                 395                 400

Ser Thr Val Glu Ala Cys Leu Pro Leu Glu Leu Thr Lys Asn Glu Ser
                405                 410                 415

Cys Leu Asn Ser Arg Glu Thr Ser Phe Ile Thr Asn Gly Ser Cys Leu
            420                 425                 430

Ala Ser Arg Lys Thr Ser Phe Met Met Ala Leu Cys Leu Ser Ser Ile
        435                 440                 445

Tyr Glu Asp Leu Lys Met Tyr Gln Val Glu Phe Lys Thr Met Asn Ala
        450                 455                 460

Lys Leu Leu Met Asp Pro Lys Arg Gln Ile Phe Leu Asp Gln Asn Met
465                 470                 475                 480

Leu Ala Val Ile Asp Glu Leu Met Gln Ala Leu Asn Phe Asn Ser Glu
                485                 490                 495

Thr Val Pro Gln Lys Ser Ser Leu Glu Glu Pro Asp Phe Tyr Lys Thr
            500                 505                 510

Lys Ile Lys Leu Cys Ile Leu Leu His Ala Phe Arg Ile Arg Ala Val
        515                 520                 525

Thr Ile Asp Arg Val Met Ser Tyr Leu Asn Ala Ser Lys Val Asp Lys
        530                 535                 540
```

-continued

```
Arg Val Glu Ser Lys Tyr Gly Pro Pro Cys Pro Ser Cys Pro Ala Pro
545                 550                 555                 560

Glu Phe Leu Gly Gly Pro Ser Val Phe Leu Phe Pro Pro Lys Pro Lys
                565                 570                 575

Asp Thr Leu Met Ile Ser Arg Thr Pro Glu Val Thr Cys Val Val Val
            580                 585                 590

Asp Val Ser Gln Glu Asp Pro Glu Val Gln Phe Asn Trp Tyr Val Asp
        595                 600                 605

Gly Val Glu Val His Asn Ala Lys Thr Lys Pro Arg Glu Glu Gln Phe
    610                 615                 620

Asn Ser Thr Tyr Arg Val Val Ser Val Leu Thr Val Leu His Gln Asp
625                 630                 635                 640

Trp Leu Asn Gly Lys Glu Tyr Lys Cys Lys Val Ser Asn Lys Gly Leu
                645                 650                 655

Pro Ser Ser Ile Glu Lys Thr Ile Ser Lys Ala Lys Gly Gln Pro Arg
            660                 665                 670

Glu Pro Gln Val Tyr Thr Leu Pro Pro Ser Pro Glu Met Thr Lys
        675                 680                 685

Asn Gln Val Ser Leu Thr Cys Leu Val Lys Gly Phe Tyr Pro Ser Asp
690                 695                 700

Ile Ala Val Glu Trp Glu Ser Asn Gly Gln Pro Glu Asn Asn Tyr Lys
705                 710                 715                 720

Thr Thr Pro Pro Val Leu Asp Ser Asp Gly Ser Phe Phe Leu Tyr Ser
                725                 730                 735

Arg Leu Thr Val Asp Lys Ser Arg Trp Gln Gln Gly Asn Val Phe Ser
            740                 745                 750

Cys Ser Val Met His Glu Ala Leu His Asn His Tyr Thr Gln Lys Ser
        755                 760                 765

Leu Ser Leu Ser Leu Gly Lys
    770                 775

<210> SEQ ID NO 2
<211> LENGTH: 781
<212> TYPE: PRT
<213> ORGANISM: Artificial Sequence
<220> FEATURE:
<223> OTHER INFORMATION: murine IL-12 IgG3 Fc fusion construct

<400> SEQUENCE: 2

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125
```

```
Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
                180                 185                 190

Glu Asp Val Thr Cys Pro Thr Ala Glu Glu Thr Leu Pro Ile Glu Leu
            195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
                260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                325                 330                 335

Gly Gly Gly Ser Gly Gly Gly Ser Gly Gly Gly Ser Arg Val
                340                 345                 350

Ile Pro Val Ser Gly Pro Ala Arg Cys Leu Ser Gln Ser Arg Asn Leu
            355                 360                 365

Leu Lys Thr Thr Asp Asp Met Val Lys Thr Ala Arg Glu Lys Leu Lys
    370                 375                 380

His Tyr Ser Cys Thr Ala Glu Asp Ile Asp His Glu Asp Ile Thr Arg
385                 390                 395                 400

Asp Gln Thr Ser Thr Leu Lys Thr Cys Leu Pro Leu Glu Leu His Lys
                405                 410                 415

Asn Glu Ser Cys Leu Ala Thr Arg Glu Thr Ser Ser Thr Thr Arg Gly
            420                 425                 430

Ser Cys Leu Pro Pro Gln Lys Thr Ser Leu Met Met Thr Leu Cys Leu
    435                 440                 445

Gly Ser Ile Tyr Glu Asp Leu Lys Met Tyr Gln Thr Glu Phe Gln Ala
    450                 455                 460

Ile Asn Ala Ala Leu Gln Asn His Asn His Gln Gln Ile Ile Leu Asp
465                 470                 475                 480

Lys Gly Met Leu Val Ala Ile Asp Glu Leu Met Gln Ser Leu Asn His
                485                 490                 495

Asn Gly Glu Thr Leu Arg Gln Lys Pro Pro Val Gly Glu Ala Asp Pro
            500                 505                 510

Tyr Arg Val Lys Met Lys Leu Cys Ile Leu Leu His Ala Phe Ser Thr
    515                 520                 525

Arg Val Val Thr Ile Asn Arg Val Met Gly Tyr Leu Ser Ser Ala Leu
    530                 535                 540
```

```
Ile Lys Arg Ile Glu Pro Arg Ile Pro Lys Pro Ser Thr Pro Pro Gly
545                 550                 555                 560

Ser Ser Cys Pro Pro Gly Asn Ile Leu Gly Gly Pro Ser Val Phe Ile
            565                 570                 575

Phe Pro Pro Lys Pro Lys Asp Ala Leu Met Ile Ser Leu Thr Pro Lys
        580                 585                 590

Val Thr Cys Val Val Val Asp Val Ser Glu Asp Pro Asp Val His
    595                 600                 605

Val Ser Trp Phe Val Asp Asn Lys Glu Val His Thr Ala Trp Thr Gln
610                 615                 620

Pro Arg Glu Ala Gln Tyr Asn Ser Thr Phe Arg Val Val Ser Ala Leu
625                 630                 635                 640

Pro Ile Gln His Gln Asp Trp Met Arg Gly Lys Glu Phe Lys Cys Lys
                645                 650                 655

Val Asn Asn Lys Ala Leu Pro Ala Pro Ile Glu Arg Thr Ile Ser Lys
                660                 665                 670

Pro Lys Gly Arg Ala Gln Thr Pro Gln Val Tyr Thr Ile Pro Pro Pro
            675                 680                 685

Arg Glu Gln Met Ser Lys Lys Lys Val Ser Leu Thr Cys Leu Val Thr
690                 695                 700

Asn Phe Phe Ser Glu Ala Ile Ser Val Glu Trp Glu Arg Asn Gly Glu
705                 710                 715                 720

Leu Glu Gln Asp Tyr Lys Asn Thr Pro Pro Ile Leu Asp Ser Asp Gly
                725                 730                 735

Thr Tyr Phe Leu Tyr Ser Lys Leu Thr Val Asp Thr Asp Ser Trp Leu
            740                 745                 750

Gln Gly Glu Ile Phe Thr Cys Ser Val Val His Glu Ala Leu His Asn
        755                 760                 765

His His Thr Gln Lys Asn Leu Ser Arg Ser Pro Gly Lys
    770                 775                 780

<210> SEQ ID NO 3
<211> LENGTH: 17
<212> TYPE: DNA
<213> ORGANISM: artificial
<220> FEATURE:
<223> OTHER INFORMATION: PCR primer

<400> SEQUENCE: 3
acacacagcc tggacgc                                                  17

<210> SEQ ID NO 4
<211> LENGTH: 20
<212> TYPE: DNA
<213> ORGANISM: artificial
<220> FEATURE:
<223> OTHER INFORMATION: PCR primer

<400> SEQUENCE: 4
catttgaact ccttgcccct                                               20

<210> SEQ ID NO 5
<211> LENGTH: 219
<212> TYPE: PRT
<213> ORGANISM: homo sapiens

<400> SEQUENCE: 5

Met Cys Pro Ala Arg Ser Leu Leu Leu Val Ala Thr Leu Val Leu Leu
1               5                   10                  15
```

```
Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
 50                  55                  60

Thr Ser Glu Glu Ile Asp His Glu Asp Ile Thr Lys Asp Lys Thr Ser
 65                  70                  75                  80

Thr Val Glu Ala Cys Leu Pro Leu Glu Leu Thr Lys Asn Glu Ser Cys
                 85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
            130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
            195                 200                 205

Ile Asp Arg Val Met Ser Tyr Leu Asn Ala Ser
            210                 215

<210> SEQ ID NO 6
<211> LENGTH: 328
<212> TYPE: PRT
<213> ORGANISM: homo sapiens

<400> SEQUENCE: 6

Met Cys His Gln Gln Leu Val Ile Ser Trp Phe Ser Leu Val Phe Leu
 1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
            130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
```

```
            165                 170                 175
Ala Glu Arg Val Arg Gly Asp Asn Lys Glu Tyr Glu Tyr Ser Val Glu
        180                 185                 190

Cys Gln Glu Asp Ser Ala Cys Pro Ala Ala Glu Glu Ser Leu Pro Ile
    195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
        260                 265                 270

Phe Cys Val Gln Val Gln Gly Lys Ser Lys Arg Glu Lys Lys Asp Arg
    275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
            325
```

```
<210> SEQ ID NO 7
<211> LENGTH: 2328
<212> TYPE: DNA
<213> ORGANISM: artificial
<220> FEATURE:
<223> OTHER INFORMATION: expression construct, coding sequence for IL-12
      IgG4 Fc fusion protein

<400> SEQUENCE: 7
atgtgtcacc agcagttggt catctcttgg ttttccctgg tttttctggc atctcccctc      60
gtggccatat gggaactgaa gaaagatgtt tatgtcgtag aattggattg gtatccggat     120
gcccctggag aaatggtggt cctcacctgt gacaccccctg aagaagatgg tatcacctgg     180
accttggacc agagcagtga ggtcttaggc tctggcaaaa ccctgaccat ccaagtcaaa     240
gagtttggag atgctggcca gtacacctgt cacaaggag gcgaggttct aagccattcg     300
ctcctgctgc ttcacaaaaa ggaagatgga atttggtcca ctgatatttt aaaggaccag     360
aaagaaccca aaaataagac ctttctaaga tgcgaggcca gaattattc tggacgtttc     420 acctgctggt ggctgacgac aatcagtact gatttgacat tcagtgtcaa agcagcaga     480 ggctcttctg accccccaagg ggtgacgtgc ggagctgcta cactctctgc agagagagtc     540 agagggaca caaggagta tgagtactca gtggagtgcc aggaggacag tgcctgccca     600
gctgctgagg agagtctgcc cattgaggtc atggtggatg ccgttcacaa gctcaagtat     660
gaaaactaca ccagcagctt cttcatcagg gacatcatca aacctgaccc acccaagaac     720
ttgcagctga agccattaaa gaattctcgg caggtggagg tcagctggga gtaccctgac     780
acctggagta ctccacattc ctacttctcc ctgacattct gcgttcaggt ccagggcaag     840
agcaagagag aaaagaaaga tagtcttc acgacaaga cctcagccac ggtcatctgc     900
cgcaaaaatg ccagcattag cgtgcgggcc caggaccgct actatagctc atcttggagc     960
gaatgggcat ctgtgccctg cagtggaggc ggtggctcgg gcggtggtgg gtcgggtggc    1020
ggcggatcca gaaacctccc cgtggccact ccagacccag gaatgttccc atgccttcac    1080
```

```
cactcccaaa acctgctgag ggccgtcagc aacatgctcc agaaggccag acaaactcta   1140
gaattttacc cttgcacttc tgaagagatt gatcatgaag atatcacaaa agataaaacc   1200
agcacagtgg aggcctgttt accattggaa ttaaccaaga atgagagttg cctaaattcc   1260
agagagacct ctttcataac taatgggagt tgcctggcct ccagaaagac ctcttttatg   1320
atggccctgt gccttagtag tatttatgaa gacttgaaga tgtaccaggt ggagttcaag   1380
accatgaatg caaagcttct gatggatcct aagaggcaga tctttctaga tcaaaacatg   1440
ctggcagtta ttgatgagct gatgcaggcc ctgaatttca cagtgagac tgtgccacaa   1500
aaatcctccc ttgaagaacc ggatttttat aaaactaaaa tcaagctctg catacttctt   1560
catgctttca gaattcgggc agtgactatt gatagagtga tgagctatct gaatgcttcc   1620
aaggtggaca agagagttga gtccaaatat ggtcccccat gcccatcatg cccagcacct   1680
gagttcctgg ggggaccatc agtcttcctg ttccccccaa acccaaggga cactctcatg   1740
atctcccgga cccctgaggt cacgtgcgtg gtggtggacg tgagccagga agaccccgag   1800
gtccagttca actggtacgt ggatggcgtg gaggtgcata atgccaagac aaagccgcgg   1860
gaggagcagt tcaacagcac gtaccgtgtg gtcagcgtcc tcaccgtcct gcaccaggac   1920
tggctgaacg gcaaggagta caagtgcaag gtctccaaca aaggcctccc gtcctccatc   1980
gagaaaacca tctccaaagc caagggcag ccccgagagc acaggtgta caccctgccc   2040
ccatccccgg aggagatgac caagaaccag gtcagcctga cctgcctggt caaaggcttc   2100
taccccagcg acatcgccgt ggagtgggag agcaatgggc agccggagaa caactacaag   2160
accacgcctc ccgtgctgga ctccgacggc tccttcttcc tctacagcag gctaaccgtg   2220
gacaagagca ggtggcagga ggggaatgtc ttctcatgct ccgtgatgca tgaggctctg   2280
cacaaccact acacacagaa gagcctctcc ctgtctctgg gtaaatga              2328
```

<210> SEQ ID NO 8
<211> LENGTH: 10994
<212> TYPE: DNA
<213> ORGANISM: artificial
<220> FEATURE:
<223> OTHER INFORMATION: plasmid vector encoding Fc tag (murine)

<400> SEQUENCE: 8

```
ctcgcagcaa agcaagatgt gtcctcagaa gctaaccatc tcctggtttg ccatcgtttt     60
gctggtgtct ccactcatgg ccatgtggga gctggagaag cttatcaaga gaatcgagcc    120
tagaataccc aagcccagta cccccccagg ttcttcatgc ccacctggta acatcttggg    180
tggaccatcc gtcttcatct tccccccaaa gcccaaggat gcactcatga tctccctaac    240
ccccaaggtt acgtgtgtgg tggtggatgt gagcgaggat gacccagatg tccatgtcag    300
ctggtttgtg gacaacaaag aagtacacac agcctggacg cagccccgtg aagctcagta    360
caacagtacc ttccgagtgg tcagtgccct cccatccag caccaggact ggatgagggg    420
caaggagttc aaatgcaagg tcaacaacaa agccctccca gccccatcg agagaaccat    480
ctcaaaaccc aaaggaagag cccagacacc tcaagtatac accataccc cacctcgtga    540
acaaatgtcc aagaagaagg ttagtctgac ctgcctggtc accaacttct ctctgaagc    600
catcagtgtg gagtgggaaa ggaacggaga actggagcag gattacaaga acactccacc    660
catcctggac tcggatggga cctacttcct ctacagcaag ctcactgtgg atacagacag    720
ttggttgcaa ggagaaattt ttacctgctc cgtggtgcat gaggctctcc ataaccacca    780
cacacagaag aacctgtctc gctcccctgg taaatgagaa cagcatctag cggccgctcg    840
```

```
aggccggcaa ggccggatcc agacatgata agatacattg atgagtttgg acaaaccaca    900
actagaatgc agtgaaaaaa atgctttatt tgtgaaattt gtgatgctat tgctttattt    960
gtaaccatta taagctgcaa taaacaagtt aacaacaaca attgcattca ttttatgttt   1020
caggttcagg gggaggtgtg ggaggttttt taaagcaagt aaaacctcta caaatgtggt   1080
atggctgatt atgatccggc tgcctcgcgc gtttcggtga tgacggtgaa aacctctgac   1140
acatgcagct cccggagacg gtcacagctt gtctgtaagc ggatgccggg agcagacaag   1200
cccgtcaggc gtcagcgggt gttggcgggt gtcgggcgc agccatgagg tcgactctag   1260
aggatcgatg ccccgccccg dacgaactaa acctgactac gacatctctg ccccttcttc   1320
gcggggcagt gcatgtaatc ccttcagttg gttggtacaa cttgccaact gggccctgtt   1380
ccacatgtga cacgggggg gaccaaacac aaagggttc tctgactgta gttgacatcc   1440
ttataaatgg atgtgcacat ttgccaacac tgagtggctt tcatcctgga gcagactttg   1500
cagtctgtgg actgcaacac aacattgcct ttatgtgtaa ctcttggctg aagctcttac   1560
accaatgctg ggggacatgt acctcccagg ggcccaggaa gactacggga ggctacacca   1620
acgtcaatca gaggggcctg tgtagctacc gataagcgga ccctcaagag ggcattagca   1680
atagtgttta taaggccccc ttgttaaccc taaacgggta gcatatgctt cccgggtagt   1740
agtatatact atccagacta accctaattc aatagcatat gttacccaac gggaagcata   1800
tgctatcgaa ttagggttag taaaagggtc ctaaggaaca gcgatatctc ccaccccatg   1860
agctgtcacg gttttattta catggggtca ggattccacg agggtagtga accatttag    1920 tcacaagggc agtggctgaa gatcaaggag cgggcagtga actctcctga atcttcgcct   1980
gcttcttcat tctccttcgt ttagctaata gaataactgc tgagttgtga acagtaaggt   2040
gtatgtgagg tgctcgaaaa caaggtttca ggtgacgccc cagaataaa atttggacgg   2100 ggggttcagt ggtggcattg tgctatgaca ccaatataac cctcacaaac cccttgggca   2160
ataaatacta gtgtaggaat gaaacattct gaatatcttt aacaatagaa atccatgggg   2220
tggggacaag ccgtaaagac tggatgtcca tctcacacga atttatggct atgggcaaca   2280
cataatccta gtgcaatatg atactggggt tattaagatg tgtcccaggc agggaccaag   2340
acaggtgaac catgttgtta cactctattt gtaacaaggg gaaagagagt ggacgccgac   2400
agcagcggac tccactggtt gtctctaaca cccccgaaaa ttaaacgggg ctccacgcca   2460
atggggccca taaacaaaga caagtggcca ctctttttt tgaaattgtg gagtgggggc   2520
acgcgtcagc ccccacacgc cgccctgcgg ttttggactg taaaataagg gtgtaataac   2580
ttggctgatt gtaaccccgc taaccactgc ggtcaaacca cttgcccaca aaaccactaa   2640 tggcacccg gggaatacct gcataagtag gtgggcgggc caagatagg gcgcgattgc    2700 tgcgatctgg aggacaaatt acacacactt gcgcctgagc gccaagcaca gggttgttgg   2760
tcctcatatt cacgaggtcg ctgagagcac ggtgggctaa tgttgccatg ggtagcatat   2820
actacccaaa tatctggata gcatatgcta tcctaatcta tatctgggta gcataggcta   2880
tcctaatcta tatctgggta gcatatgcta tcctaatcta tatctgggta gtatatgcta   2940 tcctaatttta tatctgggta gcataggcta tcctaatcta tatctgggta gcatatgcta   3000
tcctaatcta tatctgggta gtatatgcta tcctaatctg tatccgggta gcatatgcta   3060
tcctaataga gattagggta gtatatgcta tcctaattta tatctgggta gcatatacta   3120
cccaaatatc tggatagcat atgctatcct aatctatatc tgggtagcat atgctatcct   3180
```

```
aatctatatc tgggtagcat aggctatcct aatctatatc tgggtagcat atgctatcct    3240
aatctatatc tgggtagtat atgctatcct aatttatatc tgggtagcat aggctatcct    3300
aatctatatc tgggtagcat atgctatcct aatctatatc tgggtagtat atgctatcct    3360
aatctgtatc cgggtagcat atgctatcct catgcatata cagtcagcat atgataccca    3420
gtagtagagt gggagtgcta tcctttgcat atgccgccac ctcccaaggg ggcgtgaatt    3480
ttcgctgctt gtccttttcc tgctggttgc tcccattctt aggtgaattt aaggaggcca    3540
ggctaaagcc gtcgcatgtc tgattgctca ccaggtaaat gtcgctaatg ttttccaacg    3600
cgagaaggtg ttgagcgcgg agctgagtga cgtgacaaca tgggtatgcc caattgcccc    3660
atgttgggag gacgaaaatg gtgacaagac agatggccag aaatacacca acagcacgca    3720
tgatgtctac tggggattta ttctttagtg cgggggaata cacggctttt aatacgattg    3780
agggcgtctc ctaacaagtt acatcactcc tgcccttcct caccctcatc tccatcacct    3840
ccttcatctc cgtcatctcc gtcatcaccc tccgcggcag ccccttccac cataggtgga    3900
aaccagggag gcaaatctac tccatcgtca agctgcaca cagtcaccct gatattgcag    3960
gtaggagcgg gctttgtcat aacaaggtcc ttaatcgcat ccttcaaaac ctcagcaaat    4020
atatgagttt gtaaaagac catgaaataa cagacaatgg actcccttag cgggccaggt    4080
tgtgggccgg gtccaggggc cattccaaag gggagacgac tcaatggtgt aagacgacat    4140
tgtggaatag caagggcagt tcctcgcctt aggttgtaaa gggaggtctt actacctcca    4200
tatacgaaca caccggcgac ccaagttcct tcgtcggtag tcctttctac gtgactccta    4260
gccaggagag ctcttaaacc ttctgcaatg ttctcaaatt tcgggttgga acctccttga    4320
ccacgatgct ttccaaacca ccctccttt ttgcgcctgc ctccatcacc ctgaccccgg     4380
ggtccagtgc ttgggccttc tcctgggtca tctgcgggc cctgctctat cgctcccggg    4440
ggcacgtcag gctcaccatc tgggccacct tcttggtggt attcaaaata atcggcttcc    4500
cctacagggt ggaaaaatgg ccttctacct ggagggggcc tgcgcggtgg agacccggat    4560
gatgatgact gactactggg actcctgggc ctctttctc cacgtccacg acctctcccc     4620
ctggctcttt cacgacttcc cccctggct ctttcacgtc ctctaccccg cggcctcca     4680
ctacctcctc gaccccggcc tccactacct cctcgacccc ggcctccact gcctcctcga    4740
ccccggcctc cacctcctgc tcctgcccct cctgctcctg ccctcctcc tgctcctgcc     4800
cctcctgccc ctcctgctcc tgcccctcct gccctcctg ctcctgcccc tcctgccct     4860
cctgctcctg ccctcctgc ccctcctcct gctcctgccc ctcctgcccc tcctcctgct    4920
cctgcccctc ctgcccctcc tgctcctgcc cctcctgctcc tgcccctcct    4980
gccctcctg ctcctgcccc tcctgctcct gcccctcctg ctcctgcccc tcctgctcct    5040
gcccctcctg ccctcctgc ccctcctcct gctcctgccc ctcctgctcc tgcccctcct    5100
gcccctcctg ccctcctgc tcctgccct cctcctgctc ctgcccctcc tgcccctcct     5160
gcccctcctc ctgctcctgc ccctcctgcc cctcctcctg ctcctgcccc tcctgctcct    5220
cctgcccctc ctgcccctcc tgcccctcct cctgctcctg ccctcctgc ccctcctcct     5280
gctcctgccc ctcctgcct gcccctcct gccctcct gcccctcct cctgctcct        5340
gcccctcctc ctgctcctgc ccctcctgcc cctcctgccc ctcctgcccc tcctcctgct    5400
cctgcccctc ctgctcctgc ccctcctgcc cctcctgccc ctcccgctcc tgctcctgct    5460
cctgttccac cgtgggtccc tttgcagcca atgcaacttg gacgttttg gggtctccgg     5520
acaccatctc tatgtcttgg ccctgatcct gagccgcccg gggctcctgg tcttccgcct    5580
```

```
cctcgtcctc gtcctcttcc ccgtcctcgt ccatggttat caccccctct tctttgaggt    5640
ccactgccgc cggagccttc tggtccagat gtgtctccct tctctcctag gccatttcca    5700
ggtcctgtac ctggcccctc gtcagacatg attcacacta aaagagatca atagacatct    5760
ttattagacg acgctcagtg aatacaggga gtgcagactc ctgcccctc caacagcccc    5820 cccaccctca tccccttcat ggtcgctgtc agacagatcc aggtctgaaa attccccatc    5880
ctccgaacca tcctcgtcct catcaccaat tactcgcagc ccggaaaact cccgctgaac    5940
atcctcaaga tttgcgtcct gagcctcaag ccaggcctca aattcctcgt ccccttttt    6000 gctggacggt agggatgggg attctcggga cccctcctct tcctcttcaa ggtcaccaga    6060
cagagatgct actggggcaa cggaagaaaa gctgggtgcg gcctgtgagg atcagcttat    6120
cgatgataag ctgtcaaaca tgagaattct tgaagacgaa agggcctcgt gatacgccta    6180
tttttatagg ttaatgtcat gataataatg gtttcttaga cgtcaggtgg cacttttcgg    6240
ggaaatgtgc gcggaacccc tatttgttta tttttctaaa tacattcaaa tatgtatccg    6300
ctcatgagac aataaccctg ataaatgctt caataatatt gaaaaggaa gagtatgagt    6360 attcaacatt tccgtgtcgc ccttattccc tttttgcgg cattttgcct tcctgttttt    6420
gctcacccag aaacgctggt gaaagtaaaa gatgctgaag atcagttggg tgcacgagtg    6480
ggttacatcg aactggatct caacagcggt aagatccttg agagttttcg ccccgaagaa    6540
cgttttccaa tgatgagcac ttttaaagtt ctgctatgtg gcgcggtatt atcccgtgtt    6600
gacgccgggc aagagcaact cggtcgccgc atacactatt ctcagaatga cttggttgag    6660
tactcaccag tcacagaaaa gcatcttacg gatggcatga cagtaagaga attatgcagt    6720
gctgccataa ccatgagtga taacactgcg gccaacttac ttctgacaac gatcggagga    6780
ccgaaggagc taaccgcttt tttgcacaac atggggatc atgtaactcg ccttgatcgt    6840
tgggaaccgg agctgaatga agccatacca aacgacgagc gtgacaccac gatgcctgca    6900
gcaatggcaa caacgttgcg caaactatta actggcgaac tacttactct agcttcccgg    6960
caacaattaa tagactggat ggaggcggat aaagttgcag gaccacttct gcgctcggcc    7020
cttccggctg gctggtttat tgctgataaa tctggagccg gtgagcgtgg gtctcgcggt    7080
atcattgcag cactggggcc agatggtaag ccctcccgta tcgtagttat ctacacgacg    7140
gggagtcagg caactatgga tgaacgaaat agacagatcg ctgagatagg tgcctcactg    7200
attaagcatt ggtaactgtc agaccaagtt tactcatata ctttagat tgatttaaaa    7260 cttcatttt aatttaaaag gatctaggtg aagatccttt ttgataatct catgaccaaa    7320
atcccttaac gtgagttttc gttccactga gcgtcagacc ccgtagaaaa gatcaaagga    7380
tcttcttgag atcctttttt tctgcgcgta atctgctgct tgcaaacaaa aaaaccaccg    7440
ctaccagcgg tggtttgttt gccggatcaa gagctaccaa ctctttttcc gaaggtaact    7500
ggcttcagca gagcgcagat accaaatact gtccttctag tgtagccgta gttaggccac    7560
cacttcaaga actctgtagc accgcctaca tacctcgctc tgctaatcct gttaccagtg    7620
gctgctgcca gtggcgataa gtcgtgtctt accgggttgg actcaagacg atagttaccg    7680
gataaggcgc agcggtcggg ctgaacgggg ggttcgtgca cacagcccag cttggagcga    7740
acgacctaca ccgaactgag atacctacag cgtgagctat gagaaagcgc cacgcttccc    7800
gaagggagaa aggcggacag gtatccggta agcggcaggg tcggaacagg agagcgcacg    7860
agggagcttc caggggggaaa cgcctggtat ctttatagtc ctgtcgggtt tcgccacctc    7920
```

-continued

```
tgacttgagc gtcgattttt gtgatgctcg tcagggggc ggagcctatg gaaaaacgcc    7980
agcaacgcgg ccttttttacg gttcctggcc ttttgctggc cttgaagctg tccctgatgg    8040
tcgtcatcta cctgcctgga cagcatggcc tgcaacgcgg catcccgat gccgccggaa    8100
gcgagaagaa tcataatggg gaaggccatc cagcctcgcg tcgcgaacgc cagcaagacg    8160
tagcccagcg cgtcggcccc gagatgcgcc gcgtgcggct gctggagatg gcggacgcga    8220
tggatatgtt ctgccaaggg ttggtttgcg cattcacagt tctccgcaag aattgattgg    8280
ctccaattct tggagtggtg aatccgttag cgaggtgccg ccctgcttca tccccgtggc    8340
ccgttgctcg cgtttgctgg cggtgtcccc ggaagaaata tatttgcatg tctttagttc    8400
tatgatgaca caaaccccgc ccagcgtctt gtcattggcg aattcgaaca cgcagatgca    8460
gtcgggggcgg cgcggtccga ggtccacttc gcatattaag gtgacgcgtg tggcctcgaa    8520
caccgagcga ccctgcagcg acccgcttaa cagcgtcaac agcgtgccgc agatcccggg    8580
gggcaatgag atatgaaaaa gcctgaactc accgcgacgt ctgtcgagaa gtttctgatc    8640
gaaaagttcg acagcgtctc cgacctgatg cagctctcgg agggcgaaga atctcgtgct    8700
ttcagcttcg atgtaggagg gcgtggatat gtcctgcggg taaatagctg cgccgatggt    8760
ttctacaaag atcgttatgt ttatcggcac tttgcatcgg ccgcgctccc gattccggaa    8820
gtgcttgaca ttggggaatt cagcgagagc ctgacctatt gcatctcccg ccgtgcacag    8880
ggtgtcacgt tgcaagacct gcctgaaacc gaactgcccg ctgttctgca gccggtcgcg    8940
gaggccatgg atgcgatcgc tgcggccgat cttagccaga cgagcgggtt cggcccattc    9000
ggaccgcaag gaatcggtca atacactaca tggcgtgatt tcatatgcgc gattgctgat    9060
ccccatgtgt atcactggca aactgtgatg gacgacaccg tcagtgcgtc cgtcgcgcag    9120
gctctcgatg agctgatgct ttgggccgag gactgccccg aagtccggca cctcgtgcac    9180
gcggatttcg gctccaacaa tgtcctgacg gacaatggcc gcataacagc ggtcattgac    9240
tggagcgagg cgatgttcgg ggattcccaa tacgaggtcg ccaacatctt cttctggagg    9300
ccgtggttgg cttgtatgga gcagcagacg cgctacttcg agcggaggca tccggagctt    9360
gcaggatcgc cgcggctccg ggcgtatatg ctccgcattg gtcttgacca actctatcag    9420
agcttggttg acggcaattt cgatgatgca gcttgggcgc agggtcgatg cgacgcaatc    9480
gtccgatccg gagccgggac tgtcgggcgt acacaaatcg cccgcagaag cgcggccgtc    9540
tggaccgatg gctgtgtaga agtactcgcc gatagtggaa accgacgccc cagcactcgt    9600
ccggatcggg agatggggga ggctaactga aacacgaag gagacaatac cggaaggaac    9660
ccgcgctatg acggcaataa aaagacagaa taaaacgcac gggtgttggg tcgtttgttc    9720
ataaacgcgg ggttcggtcc cagggctggc actctgtcga taccccaccg agaccccatt    9780
ggggccaata cgcccgcgtt tcttcctttt ccccacccca cccccaagt tcgggtgaag    9840
gcccagggct cgcagccaac gtcggggcgg caggccctgc catagccact ggccccgtgg    9900
gttagggacg gggtcccca tggggaatgg tttatggttc gtggggtta ttattttggg    9960
cgttgcgtgg ggtcaggtcc acgactggac tgagcagaca gacccatggt ttttggatgg    10020
cctgggcatg gaccgcatgt actggcgcga cacgaacacc gggcgtctgt ggctgccaaa    10080
cacccccgac ccccaaaaac caccgcgcgg atttctggcg tgccaagcta gtcgaccaat    10140
tctcatgttt gacagcttat catcgcagat ccgggcaacg ttgttgccat tgctgcaggc    10200
gcagaactgt aggtatgga agatctatac attgaatcaa tattggcaat tagccatatt    10260
agtcattggt tatatagcat aaatcaatat tggctattgg ccattgcata cgttgtatct    10320
```

| | | | | |
|---|---|---|---|---|
| atatcataat | atgtacattt | atattggctc | atgtccaata | tgaccgccat gttgacattg | 10380 |
| attattgact | agttattaat | agtaatcaat | tacggggtca | ttagttcata gcccatatat | 10440 |
| ggagttccgc | gttacataac | ttacggtaaa | tggcccgcct | ggctgaccgc ccaacgaccc | 10500 |
| ccgcccattg | acgtcaataa | tgacgtatgt | tcccatagta | acgccaatag ggactttcca | 10560 |
| ttgacgtcaa | tgggtggagt | atttacggta | aactgcccac | ttggcagtac atcaagtgta | 10620 |
| tcatatgcca | agtccgcccc | ctattgacgt | caatgacggt | aaatgcccg cctggcatta | 10680 |
| tgcccagtac | atgaccttac | gggactttcc | tacttggcag | tacatctacg tattagtcat | 10740 |
| cgctattacc | atggtgatgc | ggttttggca | gtacaccaat | gggcgtggat agcggtttga | 10800 |
| ctcacgggga | tttccaagtc | tccaccccat | tgacgtcaat | gggagtttgt tttggcacca | 10860 |
| aaatcaacgg | gactttccaa | aatgtcgtaa | taaccccgcc | ccgttgacgc aaatgggcgg | 10920 |
| taggcgtgta | cggtgggagg | tctatataag | cagagctcgt | ttagtgaacc gtcagatctc | 10980 |
| tagaagctgg | gtac | | | | 10994 |

<210> SEQ ID NO 9
<211> LENGTH: 12539
<212> TYPE: DNA
<213> ORGANISM: artificial
<220> FEATURE:
<223> OTHER INFORMATION: plasmid vector encoding Fc-tag IL-12 fusion
      construct

<400> SEQUENCE: 9

| | | | | |
|---|---|---|---|---|
| gtacctcgca | gcaaagcaag | atgtgtcctc | agaagctaac | catctcctgg tttgccatcg | 60 |
| ttttgctggt | gtctccactc | atggccatgt | gggagctgga | gaaagacgtt tatgttgtag | 120 |
| aggtggactg | gactcccgat | gcccctggag | aaacagtgaa | cctcacctgt gacacgcctg | 180 |
| aagaagatga | catcacctgg | acctcagacc | agagacatgg | agtcataggc tctggaaaga | 240 |
| ccctgaccat | cactgtcaaa | gagttttcag | atgctggcca | gtacacctgc cacaaaggag | 300 |
| gcgagactct | gagccactca | catctgctgc | tccacaagaa | ggaaaatgga atttggtcca | 360 |
| ctgaaatttt | aaaaaatttc | aaaaacaaga | ctttcctgaa | gtgtgaagca ccaaattact | 420 |
| ccggacggtt | cacgtgctca | tggctggtgc | aaagaaacat | ggacttgaag ttcaacatca | 480 |
| agagcagtag | cagttcccct | gactctcggg | cagtgacatg | tggaatggcg tctctgtctg | 540 |
| cagagaaggt | cacactggac | caaagggact | atgagaagta | ttcagtgtcc tgccaggagg | 600 |
| atgtcacctg | cccaactgcc | gaggagaccc | tgcccattga | actggcgttg gaagcacggc | 660 |
| agcagaataa | atatgagaac | tacagcacca | gcttcttcat | cagggacatc atcaaaccag | 720 |
| acccgcccaa | gaacttgcag | atgaagcctt | tgaagaactc | acaggtggag tcagctgggg | 780 |
| agtaccctga | ctcctggagc | actccccatt | cctacttctc | cctcaagttc tttgttcgaa | 840 |
| tccagcgcaa | gaaagaaaag | atgaaggaga | cagaggaggg | tgtaaccag aaaggtgcgt | 900 |
| tcctcgtaga | gaagacatct | accgaagtcc | aatgcaaagg | cgggaatgtc tgcgtgcaag | 960 |
| ctcaggatcg | ctattacaat | tcctcgtgca | gcaagtgggc | atgtgttccc tgcagggtcc | 1020 |
| gatccggagc | cggtggctcg | ggcggtggtg | gtcgggtgg cggcggatcc agggtcattc | | 1080 |
| cagtctctgg | acctgccagg | tgtcttagcc | agtcccgaaa | cctgctgaag accacagatg | 1140 |
| acatggtgaa | gacggccaga | gaaaaactga | acattattc | ctgcactgct gaagacatcg | 1200 |
| atcatgaaga | catcacacgg | gaccaaacca | gcacattgaa | gacctgttta ccactggaac | 1260 |
| tacacaagaa | cgagagttgc | ctggctacta | gagagacttc | ttccacaaca agagggagct | 1320 |

```
gcctgccccc acagaagacg tctttgatga tgaccctgtg ccttggtagc atctatgagg    1380
acttgaagat gtaccagaca gagttccagg ccatcaacgc agcacttcag aatcacaacc    1440
atcagcagat cattctagac aagggcatgc tggtggccat cgatgagctg atgcagtctc    1500
tgaatcataa tggcgagact ctgcgccaga aacctcctgt gggagaagca gacccttaca    1560
gagtgaaaat gaagctctgc atcctgcttc acgccttcag cacccgcgtc gtgaccatca    1620
acagggtgat gggctatctg agctccgcct tgatcaagag aatcgagcct agaatacccA    1680
agcccagtac ccccccaggt tcttcatgcc cacctggtaa catcttgggt ggaccatccg    1740
tcttcatctt cccccccaaag cccaaggatg cactcatgat ctccctaacc cccaaggtta    1800
cgtgtgtggt ggtggatgtg agcgaggatg acccagatgt ccatgtcagc tggtttgtgg    1860
acaacaaaga agtacacaca gcctggacgc agccccgtga agctcagtac aacagtacct    1920
tccgagtggt cagtgccctc cccatccagc accaggactg gatgaggggc aaggagttca    1980
aatgcaaggt caacaacaaa gccctcccag ccccatcga gagaaccatc tcaaaaccca    2040
aaggaagagc ccagacacct caagtataca ccatacccCC acctcgtgaa caaatgtcca    2100
agaagaaggt tagtctgacc tgcctggtca ccaacttctt ctctgaagcc atcagtgtgg    2160
agtgggaaag gaacggagaa ctggagcagg attacaagaa cactccaccc atcctggact    2220
cggatgggac ctacttcctc tacagcaagc tcactgtgga tacagacagt tggttgcaag    2280
gagaaatttt tacctgctcc gtggtgcatg aggctctcca taaccaccac acacagaaga    2340
acctgtctcg ctcccctggt aaatgagaac agcatctagc ggccgctcga ggccggcaag    2400
gccggatcca gacatgataa gatacattga tgagtttgga caaaccacaa ctagaatgca    2460
gtgaaaaaaa tgctttattt gtgaaatttg tgatgctatt gctttatttg taaccattat    2520
aagctgcaat aaacaagtta caacaacaa ttgcattcat tttatgtttc aggttcaggg    2580
ggaggtgtgg gaggtttttt aaagcaagta aaacctctac aaatgtggta tggctgatta    2640
tgatccggct gcctcgcgcg tttcggtgat gacggtgaaa acctctgaca catgcagctc    2700
ccggagacgg tcacagcttg tctgtaagcg gatgccggga gcagacaagc ccgtcaggcg    2760
tcagcgggtg ttggcgggtg tcggggcgca gccatgaggt cgactctaga ggatcgatgc    2820
cccgccccgg acgaactaaa cctgactacg acatctctgc cccttcttcg cggggcagtg    2880
catgtaatcc cttcagttgg ttggtacaac ttgccaactg ggccctgttc cacatgtgac    2940
acgggggggg accaaacaca aaggggttct ctgactgtag ttgacatcct tataaatgga    3000
tgtgcacatt tgccaacact gagtggcttt catcctggag cagactttgc agtctgtgga    3060
ctgcaacaca acattgcctt tatgtgtaac tcttggctga agctcttaca ccaatgctgg    3120
gggacatgta cctcccaggg gcccaggaag actacgggag gctacaccaa cgtcaatcag    3180
aggggcctgt gtagctaccg ataagcggac cctcaagagg gcattagcaa tagtgtttat    3240
aaggccccct tgttaaccct aaacgggtag catatgcttc ccgggtagta gtatatacta    3300
tccagactaa ccctaattca atagcatatg ttacccaacg ggaagcatat gctatcgaat    3360
tagggttagt aaaagggtcc taaggaacag cgatatctcc cacccccatga gctgtcacgg    3420
ttttatttac atgggtcag gattccacga gggtagtgaa ccattttagt cacaagggca    3480
gtggctgaag atcaaggagc gggcagtgaa ctctcctgaa tcttcgcctg cttcttcatt    3540
ctccttcgtt tagctaatag aataaactgct gagttgtgaa cagtaaggtg tatgtgaggt    3600
gctcgaaaac aaggtttcag gtgacgcccc cagaataaaa tttggacggg gggttcagtg    3660
```

-continued

```
gtggcattgt gctatgacac caatataacc ctcacaaacc ccttgggcaa taaatactag    3720
tgtaggaatg aaacattctg aatatcttta acaatagaaa tccatggggt ggggacaagc    3780
cgtaaagact ggatgtccat ctcacacgaa tttatggcta tgggcaacac ataatcctag    3840
tgcaatatga tactggggtt attaagatgt gtcccaggca gggaccaaga caggtgaacc    3900
atgttgttac actctatttg taacaagggg aaagagagtg gacgccgaca gcagcggact    3960
ccactggttg tctctaacac ccccgaaaat taaacggggc tccacgccaa tggggcccat    4020
aaacaaagac aagtggccac tcttttttt gaaattgtgg agtggggca cgcgtcagcc      4080 cccacacgcc gccctgcggt tttggactgt aaaataaggg tgtaataact tggctgattg    4140 taacccccgct aaccactgcg gtcaaaccac ttgcccacaa aaccactaat ggcaccccgg   4200
ggaatacctg cataagtagg tgggcgggcc aagatagggg cgcgattgct gcgatctgga   4260
ggacaaatta cacacacttg cgcctgagcg ccaagcacag ggttgttggt cctcatattc    4320
acgaggtcgc tgagagcacg gtgggctaat gttgccatgg gtagcatata ctacccaaat   4380
atctggatag catatgctat cctaatctat atctgggtag cataggctat cctaatctat    4440
atctgggtag catatgctat cctaatctat atctgggtag tatatgctat cctaatttat    4500
atctgggtag cataggctat cctaatctat atctgggtag catatgctat cctaatctat    4560
atctgggtag tatatgctat cctaatctgt atccgggtag catatgctat cctaatagag    4620
attagggtag tatatgctat cctaatttat atctgggtag catatactac ccaaatatct    4680
ggatagcata tgctatccta atctatatct gggtagcata tgctatccta atctatatct    4740
gggtagcata ggctatccta atctatatct gggtagcata tgctatccta atctatatct    4800
gggtagtata tgctatccta atttatatct gggtagcata ggctatccta atctatatct    4860
gggtagcata tgctatccta atctatatct gggtagtata tgctatccta atctgtatcc    4920
gggtagcata tgctatcctc atgcatatac agtcagcata tgatacccag tagtagagtg    4980
ggagtgctat cctttgcata tgccgccacc tcccaagggg gcgtgaattt tcgctgcttg    5040
tccttttcct gctggttgct cccattctta ggtgaattta aggaggccag gctaaagccg    5100
tcgcatgtct gattgctcac caggtaaatg tcgctaatgt tttccaacgc gagaaggtgt    5160
tgagcgcgga gctgagtgac gtgacaacat gggtatgccc aattgcccca tgttgggagg    5220
acgaaaatgg tgacaagaca gatggccaga aatacaccaa cagcacgcat gatgtctact    5280
ggggatttat tctttagtgc gggggaatac acggcttta atacgattga gggcgtctcc     5340
taacaagtta catcactcct gcccttcctc accctcatct ccatcacctc cttcatctcc    5400
gtcatctccg tcatcaccct ccgcggcagc cccttccacc ataggtggaa accagggagg    5460
caaatctact ccatcgtcaa agctgcacac agtcaccctg atattgcagg taggagcggg    5520
ctttgtcata acaaggtcct taatcgcatc cttcaaaacc tcagcaaata tatgagtttg    5580
taaaaagacc atgaaataac agacaatgga ctcccttagc gggccaggtt gtgggccggg    5640
tccaggggcc attccaaagg ggagacgact caatggtgta agacgacatt gtggaatagc    5700
aagggcagtt cctcgcctta ggttgtaaag ggaggtctta ctacctccat atacgaacac    5760
accggcgacc caagttcctt cgtcggtagt cctttctacg tgactcctag ccaggagagc    5820
tcttaaacct tctgcaatgt tctcaaattt cgggttggaa cctccttgac cacgatgctt    5880
tccaaaccac cctccttttt tgcgcctgcc tccatcaccc tgaccccggg gtccagtgct    5940
tgggccttct cctgggtcat ctgcggggcc ctgctctatc gctcccgggg gcacgtcagg    6000
ctcaccatct gggccaccct cttggtggta ttcaaaataa tcggcttccc ctacagggtg    6060
```

```
gaaaaatggc cttctacctg gagggggcct gcgcggtgga gacccggatg atgatgactg    6120
actactggga ctcctgggcc tcttttctcc acgtccacga cctctccccc tggctctttc    6180
acgacttccc ccctggctc tttcacgtcc tctaccccgg cggcctccac tacctcctcg    6240
accccggcct ccactacctc ctcgaccccg gcctccactg cctcctcgac cccggcctcc    6300
acctcctgct cctgcccctc ctgctcctgc ccctcctcct gctcctgccc ctcctgcccc    6360
tcctgctcct gcccctcctg cccctcctgc tcctgcccct cctgcccctc ctgctcctgc    6420
ccctcctgcc cctcctcctg ctcctgcccc tcctgcccct cctgctc ctgcccctcc    6480 tgcccctcct gctcctgccc ctcctgcccc tcctgctcct gcccctcctg cccctcctgc    6540
tcctgcccct cctgctcctg ccctcctgc tcctgcccct cctgctcctg ccctcctgc    6600 ccctcctgcc cctcctcctg ctcctgcccc tcctgctcct gcccctcctg ccctcctgc    6660 ccctcctgct cctgcccctc ctgctcctgc tgcccctcct gcccctcctg ccctcctcc    6720 tgctcctgcc cctcctgccc ctcctgc tcctgcccct cctgctc ctgcccctcc    6780 tgcccctcct gcccctcctc ctgctcctgc cctcctgcc cctcctgc tcctgcccc    6840 tcctcctgct cctgcccctc ctgcccctcc tgcccctcct cctgctcctg ccctcctcc    6900 tgctcctgcc cctcctgccc ctcctgcccc tcctgcccct cctgctc ctgcccctcc    6960 tcctgctcct gcccctcctg ctcctgcccc tcccgctcct gctcctgctc ctgttccacc    7020
gtgggtccct ttgcagccaa tgcaacttgg acgttttgg ggtctccgga caccatctct    7080
atgtcttggc cctgatcctg agccgccgg ggctcctggt cttccgcctc ctcgtcctcg    7140
tcctcttccc cgtcctcgtc catggttatc accccctctt ctttgaggtc cactgccgcc    7200
ggagccttct ggtccagatg tgtctcccttt ctctcctagg ccatttccag gtcctgtacc    7260
tggcccctcg tcagacatga ttcacactaa aagagatcaa tagacatctt tattagacga    7320
cgctcagtga atacagggag tgcagactcc tgcccctcc aacagccccc ccaccctcat    7380 cccttcatg gtcgctgtca gacagatcca ggtctgaaaa ttccccatcc tccgaaccat    7440
cctcgtcctc atcaccaatt actcgcagcc cggaaaactc ccgctgaaca tcctcaagat    7500
ttgcgtcctg agcctcaagc caggcctcaa attcctcgtc cccctttttg ctggacggta    7560
gggatgggga ttctcgggac ccctcctctt cctcttcaag gtcaccagac agagatgcta    7620
ctggggcaac ggaagaaaag ctgggtgcgg cctgtgagga tcagcttatc gatgataagc    7680
tgtcaaacat gagaattctt gaagacgaaa gggcctcgtg atacgcctat ttttataggt    7740
taatgtcatg ataataatgg tttcttagac gtcaggtggc acttttcggg gaaatgtgcg    7800 cggaaccct atttgtttat ttttctaaat acattcaaat atgtatccgc tcatgagaca    7860
ataaccctga taaatgcttc aataatattg aaaaggaag agtatgagta ttcaacattt    7920
ccgtgtcgcc cttattccct tttttgcggc attttgcctt cctgttttg ctcacccaga    7980 aacgctggtg aaagtaaaag atgctgaaga tcagttgggt gcacgagtgg gttacatcga    8040
actggatctc aacagcggta agatccttga gagttttcgc cccgaagaac gttttccaat    8100
gatgagcact ttaaagttc tgctatgtgg cgcggtatta tcccgtgttg acgccgggca    8160
agagcaactc ggtcgccgca tacactattc tcagaatgac ttggttgagt actcaccagt    8220
cacagaaaag catcttacgg atggcatgac agtaagagaa ttatgcagtg ctgccataac    8280
catgagtgat aacactgcgg ccaacttact tctgacaacg atcggaggac cgaaggagct    8340
aaccgctttt ttgcacaaca tggggatca tgtaactcgc cttgatcgtt gggaaccgga    8400
```

```
gctgaatgaa gccataccaa acgacgagcg tgacaccacg atgcctgcag caatggcaac    8460
aacgttgcgc aaactattaa ctggcgaact acttactcta gcttcccggc aacaattaat    8520
agactggatg gaggcggata aagttgcagg accacttctg cgctcggccc ttccggctgg    8580
ctggtttatt gctgataaat ctggagccgg tgagcgtggg tctcgcggta tcattgcagc    8640
actggggcca gatggtaagc cctcccgtat cgtagttatc tacacgacgg ggagtcaggc    8700
aactatggat gaacgaaata gacagatcgc tgagataggt gcctcactga ttaagcattg    8760
gtaactgtca gaccaagttt actcatatat actttagatt gatttaaaac ttcatttttta   8820 atttaaaagg atctaggtga agatcctttt tgataatctc atgaccaaaa tcccttaacg    8880
tgagttttcg ttccactgag cgtcagaccc cgtagaaaag atcaaaggat cttcttgaga    8940 tcctttttt ctgcgcgtaa tctgctgctt gcaaacaaaa aaccaccgc taccagcggt      9000 ggtttgtttg ccggatcaag agctaccaac tcttttttccg aaggtaactg gcttcagcag   9060
agcgcagata ccaaatactg tccttctagt gtagccgtag ttaggccacc acttcaagaa    9120
ctctgtagca ccgcctacat acctcgctct gctaatcctg ttaccagtgg ctgctgccag    9180
tggcgataag tcgtgtctta ccgggttgga ctcaagacga tagttaccgg ataaggcgca    9240
gcggtcgggc tgaacgggg gttcgtgcac acagcccagc ttggagcgaa cgacctacac      9300
cgaactgaga tacctacagc gtgagctatg agaaagcgcc acgcttcccg aagggagaaa    9360
ggcggacagg tatccggtaa gcggcagggt cggaacagga gagcgcacga gggagcttcc    9420
agggggaaac gcctggtatc tttatagtcc tgtcgggttt cgccacctct gacttgagcg    9480
tcgatttttg tgatgctcgt caggggggcg gagcctatgg aaaaacgcca gcaacgcggc    9540
ctttttacgg ttcctggcct tttgctggcc ttgaagctgt ccctgatggt cgtcatctac    9600
ctgcctggac agcatggcct gcaacgcggg catcccgatg ccgccggaag cgagaagaat    9660
cataatgggg aaggccatcc agcctcgcgt cgcgaacgcc agcaagacgt agcccagcgc    9720 gtcggcccg agatgcgccg cgtgcggctg ctggagatgg cggacgcgat ggatatgttc     9780
tgccaagggt tggtttgcgc attcacagtt ctccgcaaga attgattggc tccaattctt    9840
ggagtggtga atccgttagc gaggtgccgc cctgcttcat ccccgtgcc cgttgctcgc     9900 gtttgctggc ggtgtccccg gaagaaatat atttgcatgt ctttagttct atgatgacac    9960
aaaccccgcc cagcgtcttg tcattggcga attcgaacac gcagatgcag tcggggcggc    10020
gcggtccgag gtccacttcg catattaagg tgacgcgtgt ggcctcgaac accgagcgac    10080
cctgcagcga cccgcttaac agcgtcaaca gcgtgccgca gatcccgggg gcaatgaga    10140 tatgaaaaag cctgaactca ccgcgacgtc tgtcgagaag tttctgatcg aaaagttcga    10200
cagcgtctcc gacctgatgc agctctcgga gggcgaagaa tctcgtgctt tcagcttcga    10260
tgtaggaggg cgtggatatg tcctgcgggt aaatagctgc gccgatggtt tctacaaaga    10320
tcgttatgtt tatcggcact ttgcatcggc cgcgctcccg attccggaag tgcttgacat    10380
tggggaattc agcgagagcc tgacctattg catctcccgc cgtgcacagg gtgtcacgtt    10440
gcaagacctg cctgaaaccg aactgcccgc tgttctgcag ccggtcgcgg aggccatgga    10500
tgcgatcgct gcggccgatc ttagccagac gagcgggttc ggcccattcg gaccgcaagg    10560
aatcggtcaa tacactacat ggcgtgattt catatgcgcg attgctgatc cccatgtgta    10620
tcactggcaa actgtgatgg acgacaccgt cagtgcgtcc gtcgcgcagg ctctcgatga    10680
gctgatgctt tgggccgagg actgccccga agtccggcac ctcgtgcacg cggatttcgg    10740
ctccaacaat gtcctgacgg acaatggccg cataacagcg gtcattgact ggagcgaggc    10800
```

-continued

```
gatgttcggg gattcccaat acgaggtcgc caacatcttc ttctggaggc cgtggttggc    10860
ttgtatggag cagcagacgc gctacttcga gcggaggcat ccggagcttg caggatcgcc    10920
gcggctccgg gcgtatatgc tccgcattgg tcttgaccaa ctctatcaga gcttggttga    10980
cggcaatttc gatgatgcag cttgggcgca gggtcgatgc gacgcaatcg tccgatccga    11040
agccgggact gtcgggcgta cacaaatcgc ccgcagaagc gcggccgtct ggaccgatgg    11100
ctgtgtagaa gtactcgccg atagtggaaa ccgacgcccc agcactcgtc cggatcggga    11160 gatggggggag gctaactgaa acacggaagg agacaatacc ggaaggaacc cgcgctatga   11220
cggcaataaa aagacagaat aaaacgcacg ggtgttgggt cgtttgttca taaacgcggg    11280
gttcggtccc agggctggca ctctgtcgat accccaccga gaccccattg gggccaatac    11340
gcccgcgttt cttccttttc cccacccccac ccccaagtt cgggtgaagg cccagggctc    11400
gcagccaacg tcgggcggc aggccctgcc atagccactg gccccgtggg ttaggggacgg    11460 ggtcccccat ggggaatggt ttatggttcg tgggggttat tattttgggc gttgcgtggg    11520
gtcaggtcca cgactggact gagcagacag acccatggtt tttggatggc ctgggcatgg    11580
accgcatgta ctggcgcgac acgaacaccg ggcgtctgtg gctgccaaac acccccgacc    11640
cccaaaaacc accgcgcgga tttctggcgt gccaagctag tcgaccaatt ctcatgtttg    11700
acagcttatc atcgcagatc cgggcaacgt tgttgccatt gctgcaggcg cagaactggt    11760
aggtatggaa gatctataca ttgaatcaat attggcaatt agccatatta gtcattggtt    11820
atatagcata aatcaatatt ggctattggc cattgcatac gttgtatcta tatcataata    11880
tgtacattta tattggctca tgtccaatat gaccgccatg ttgacattga ttattgacta    11940
gttattaata gtaatcaatt acggggtcat tagttcatag cccatatatg gagttccgcg    12000
ttacataact tacggtaaat ggcccgcctg gctgaccgcc caacgacccc cgcccattga    12060
cgtcaataat gacgtatgtt cccatagtaa cgccaatagg gactttccat tgacgtcaat    12120
gggtggagta tttacggtaa actgcccact tggcagtaca tcaagtgtat catatgccaa    12180
gtccgccccc tattgacgtc aatgacggta aatggcccgc ctggcattat gcccagtaca    12240
tgaccttacg ggactttcct acttggcagt acatctacgt attagtcatc gctattacca    12300
tggtgatgcg gttttggcag tacaccaatg ggcgtggata gcggtttgac tcacggggat    12360
ttccaagtct ccacccccatt gacgtcaatg ggagtttgtt ttggcaccaa aatcaacggg    12420
actttccaaa atgtcgtaat aaccccgccc cgttgacgca aatgggcggt aggcgtgtac    12480
ggtgggaggt ctatataagc agagctcgtt tagtgaaccg tcagatctct agaagctgg    12539
```

METHODS OF TREATING MALIGNANT TUMOUR WITH IL-12 AND ANTI-PD-1 ANTIBODY

CROSS-REFERENCE TO RELATED APPLICATIONS

This is a Continuation-in-Part of U.S. patent application Ser. No. 14/350,362, filed Apr. 8, 2014, which is the US National Stage of International Application No. PCT/EP2012/070088 filed Oct. 10, 2012; which in turn claims the benefit of U.S. Provisional Patent Application No. 61/573,200, filed Nov. 14, 2011; European Patent Application No. EP11184644.0, filed on Oct. 11, 2011; European Patent Application No. EP 11188625.5, filed on Nov. 10, 2011; and European Patent Application No. EP 12185108.3, filed on Sep. 19, 2012. The contents of the foregoing patent applications are incorporated by reference herein in their entirety.

FIELD

This disclosure relates to compositions and methods for treating cancer, in particular, to immunotherapy of malignant neoplastic disease such as glioma, by administering an effective dose of a polypeptide with IL-12 biological activity and a non-agonist ligand of a T-cell down-regulator, particularly a non-agonist ligand to CTLA-4 and/or to Programmed Death 1 (PD-1).

BACKGROUND

Glioblastoma multiforme (GBM) is the most malignant astrocytic tumour. GBM exhibits an invasive and destructive growth pattern; it is the most common and most aggressive malignant primary brain tumour in humans, accounting for 20% of all intracranial tumours. In most European countries and North America, GBM incidence is in the range of 3-3.5 new cases per 100,000 population per year. The clinical history of the disease is usually short (less than 3 months in more than 50% of cases) and patients diagnosed with GBM show a median survival of 14-18 months despite aggressive surgery, radiation, and chemotherapy. The ability of gliomas to withstand conventional treatment regimens is one of the greatest challenges of modern neuro-oncology.

Interleukin (IL)-12 is the prototype of a group of heterodimeric cytokines with predominantly inflammatory properties. IL-12 polarizes naive helper T-cells to adopt a TH1 phenotype and stimulates cytotoxic T and NK-cells. IL-12 binds to the IL-12 receptor (IL-12R), which is a heterodimeric receptor formed by IL-12R-β1 and IL-12R-β2. The receptor complex is primarily expressed by T cells, but also other lymphocyte subpopulations have been found to be responsive to IL-12.

The therapeutic application of IL-12 in various tumour entities has been suggested. Clinical trials in cancer patients, however, had to be halted since systemic application evoked serious adverse events at effective doses, including fatalities. While research in recent years has mainly focused on various administration routes of IL-12, there remain open questions on the exact mechanisms by which IL-12 exerts its tumour-suppressive properties.

CTLA-4 and PD-1 are both members of the extended CD28/CTLA-4 family of T cell regulators. PD-1 is expressed on the surface of activated T cells, B cells and macrophages. PD-1 (CD279; Uniprot Q15116) has two ligands, PD-L1 (B7-H1, CD274) and PD-L2 (B7-DC, CD273), which are members of the B7 family.

CTLA-4 (Uniprot ID No P16410) is expressed on the surface of T helper cells and transmits an inhibitory signal to T lymphocytes. CTLA-4 and CD28 bind to CD80 (B7-1) and CD86 (B7-2) on antigen-presenting cells. CTLA-4 transmits an inhibitory signal to T cells, whereas CD28 transmits a stimulatory signal. Systemic anti-CTLA-4 treatment has been approved for clinical use and demonstrates clinical benefit. It is being further tested for various other solid cancers (Hodi et al., *N Engl J Med* 363, 711-723 (2010); Graziani et al., *Pharmacol Res* (2012) January; 65(1):9-22). A commercial antibody against CTLA-4 is available under the generic name ipilimumab (marketed as Yervoy). Another commercial antibody against CTLA-4 is tremelimumab (CAS number 745013-59-6).

Various anti-PD-L1 antibodies (e.g. MDX-1105/BMS-936559) and anti-PD-1 antibodies are currently undergoing clinical trials or have been approved for human use (e.g. Nivolumab (CAS No. 946414-94-4; MDX-1106/BMS-936558/ONO-4538), pembrolizumab (CAS No. 1374853-91-4; MK-3475/SCH 900475), cemiplimab (CAS No 1801342-60-8), atezlizumab (CAS No. 1380723-44-3), avelumab (CAS No. 1537032-82-8), durvalumab (CAS No. 1428935-60-7) or AMP-224 (GSK)).

The glycoprotein immunoglobulin G (IgG) is a major effector molecule of the humoral immune response in man. There are four distinct subgroups of human IgG designated IgG1, IgG2, IgG3 and IgG4. The four subclasses show more than 95% homology in the amino acid sequences of the constant domains of the heavy chains, but differ with respect to structure and flexibility of the hinge region, especially in the number of inter-heavy chain disulfide bonds in this domain. The structural differences between the IgG subclasses are also reflected in their susceptibility to proteolytic enzymes, such as papain, plasmin, trypsin and pepsin.

Only one isoform of human IgG4 is known. In contrast to human IgG1, IgG2 and IgG3, human IgG4 does not activate complement. Furthermore, IgG4 is less susceptible to proteolytic enzymes compared to IgG2 and IgG3.

The problem underlying the present invention is the provision of improved means and methods for treating solid cancer, in particular glioma.

SUMMARY

Described herein are methods of treating a patient suffering from a malignant primary tumor such as glioma and glioblastoma multiform; including the administering into a malignant primary tumor, into the vicinity of a malignant primary tumor, or to the lymph node associated with a malignant primary tumor, an effective amount of a recombinant IL-12 polypeptide or a polypeptide comprising a polypeptide sequence at least 95% identical to the sequence of human p35 (SEQ ID NO:5), and a polypeptide sequence at least 95% identical to the sequence of human p40 (SEQ ID NO:6) and a human immunoglobulin G crystallisable fragment; and the systemic administration of an effective amount of a non-agonist CTLA-4 antibody, thereby treating the malignant primary tumor.

BRIEF DESCRIPTION OF THE DRAWINGS

FIG. 4A) G1261 IL-12Fc were implanted in mice lacking T and B cells (Rag1$^{-/-}$) or NK cells (Il-15ra$^{-/-}$) or lacking both T-, B-, NK cells and lymphoid tissue inducer like cells (Rag2$^{-/-}$ Il2rg$^{-/-}$). FIG. 4B) IL-12Fc were implanted in mice deficient for MHCII (Ia(b)$^{-/-}$) and MHCI (β2m$^{-/-}$), $^{(n=}$5-8 mice/group), lacking CD4 or CD8 positive T-cells, respectively. Data are representative of 2 independent experiments.

FIG. 6A) wt (open circles) and IFNγ$^{-/-}$ (black circles) animals FIG. 6B) wt (open circles) and Perforin$^{-/-}$ (black circles) animals. Quantification of tumour growth which correlates to photon flux (p/s) in the region of interest (ROI) versus the days post injection of the modified glioma cells are shown (upper panel). Lower panel: Kaplan-Meier survival analysis. Data are representative of 2 independent experiments.

Figure 1A:
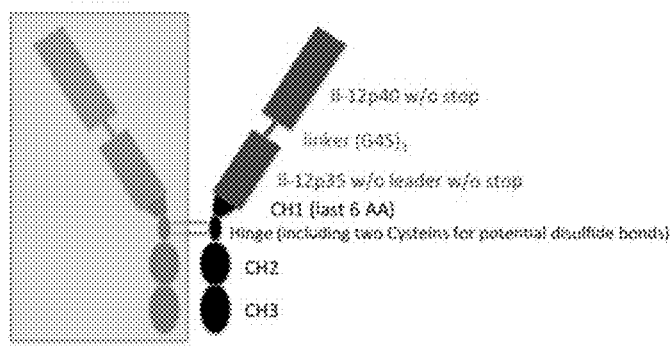
FIG. 1a shows the structure and sequence of the fusion protein given in SEQ ID 01. The subunits p40 and p35 of IL-12 are depicted as rectangles. These subunits are connected by a linker ($G_4S_3$. The subunits CH2, CH3 and the last six amino acids of CH1 of the crystallizable fragment of the immunoglobulin are shown as oblong circles.

Systemic treatment: at day 21 (arrow), tumor bearing animals were treated initially with 200 µg αCTLA-4 mouse IgG2b (9D9) (filled light grey triangles, n=8), 200 ng of recombinant heterodimeric IL-12 (rIL-12) (filled dark grey triangles, n=9) or a combination of both (filled black triangles, n=9) injected intraperitoneal (i.p.). The control group received phospate buffered saline (PBS) (filled open triangles, n=7). Treatment was sustained with 100 µg αCTLA-4 or 100 ng rIL-12 or a combination of both 3 times/week until the end of the experiment. Upper graph: quantification of ROI photon flux of tumor bearing wt animals receiving the indicated treatment. Lower graph: Kaplan-Meier survival analysis of the animals above; Log-rank (Mantel-Cox) Test was used to calculate the p-values indicated; Pooled data from two independent experiments.

BRIEF DESCRIPTION OF THE DESCRIBED SEQUENCES

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 95083_303_1001_seq, about 53 KB. In the Sequence Listing:

SEQ ID NO: 1 is the amino acid sequence of a human fusion protein IL-12Fc.

SEQ ID NO: 2 is the amino acid sequence of a murine IL-12 IgG3 Fc fusion construct.

SEQ ID NO: 3 is the nucleic acid forward primer of IgG3fw: acacacagcctggacgc

SEQ ID NO: 4 is the nucleic acid reverse primer of IgG3rev: catttgaactccttgcccct SEQ ID NO: 5 is the amino acid sequence of p35 polypeptide.

SEQ ID NO: 6 is the amino acid sequence of p40 polypeptide.

SEQ ID NO: 7 is the nucleic acid sequence expression construct, coding sequence for IL-12 IgG4 Fc fusion.

SEQ ID NO: 8 is the nucleic acid sequence of plasmid vector encoding Fc tag (murine).

SEQ ID NO: 9 is the nucleic acid sequence of plasmid vector encoding Fc-tag IL-12 fusion construct.

DETAILED DESCRIPTION

I. Overview of Several Embodiments

Described herein are methods of treating a patient suffering from a malignant primary tumor such as glioma and glioblastoma multiform; including the administering into a malignant primary tumor, into the vicinity of a malignant primary tumor, or to the lymph node associated with a malignant primary tumor, an effective amount of a recombinant IL-12 polypeptide or a polypeptide comprising a polypeptide sequence at least 95% identical to the sequence of human p35 (SEQ ID NO:5), and a polypeptide sequence at least 95% identical to the sequence of human p40 (SEQ ID NO:6) and a human immunoglobulin G crystallisable fragment; and the systemic administration of an effective amount of a non-agonist CTLA-4 antibody, thereby treating the malignant primary tumor.

In some embodiments the recombinant IL-12 polypeptide comprises a human immunoglobulin G subgroup 4 crystallisable fragment.

In particular embodiments the recombinant IL-12 polypeptide includes an immunoglobulin G crystallisable fragment and a recombinant or synthetic human IL-12 sequence, or a sequence at least 95% identical to SEQ ID NO:1.

In some embodiments the non-agonist CTLA-4 antibody is a gamma immunoglobulin that binds to CTLA-4.

In particular embodiments the recombinant IL-12 polypeptide is provided as a dosage form for intratumoural injection.

In some embodiments the non-agonist CTLA-4 antibody is provided as a dosage form for intravenous injection.

In further embodiments the recombinant IL-12 polypeptide is a fusion protein including the human p40 p35 subunits and the crystallisable fragment of human IgG4, said recombinant IL-12 polypeptide is provided as a dosage form for intratumoural delivery, and wherein said non-agonist CTLA-4 antibody is an immunoglobulin G provided as a dosage form for systemic delivery.

In particular embodiments the malignant primary tumor is glioblastoma multiforme.

In some embodiments the method of treatment is a method of inhibiting growth of the malignant primary tumor. In other embodiments the treatment is a method of reducing the size of the malignant primary tumor.

II. Detailed Description of the Embodiments

In the course of a study focused on the clinical therapeutic potential or IL-12 in advanced-stage GBM in a relevant rodent model, it was surprisingly found that the combination of IL-12 with a blockade of co-inhibitory signals with anti-CTLA-4 antibody leads to almost complete tumour eradication and cure even at advanced disease stages. The combination of IL-12 with a blockade of co-inhibitory signals with anti-PD-1 antibody as well leads to tumour regression.

According to a first aspect of the invention, a combination medicament is provided for use in the therapy of solid tumours, particular brain tumours, particularly glioma, which comprises
an IL-12 polypeptide and
a T cell inhibition blocker agent selected from
a non-agonist CTLA-4 ligand and
a non-agonist PD-1 or PD-L1 or PD-L2 ligand.

In the context of the present invention, an IL-12 polypeptide is a polypeptide having an amino acid sequence comprising the sequence of p35 (Uniprot ID 29459, SEQ ID 05) or a functional homologue thereof, and comprising the sequence of p40 (Uniprot ID29460, SEQ ID 06) or a functional homologue thereof. In one embodiment, the IL-12 polypeptide has an amino acid sequence comprising both p35 and p40 sequences or homologues thereof as part of the same continuous amino acid chain. In another embodiment, the IL-12 polypeptide comprises two distinct amino acid chains, one comprising the p35 sequence and another one comprising the p40 sequence. The terminology "IL-12 polypeptide" does not preclude the presence of non-IL-12 sequences, for example immunoglobulin sequences and fragments thereof, fused to the IL-12 sequences described herein.

The IL-12 polypeptide has a biological activity of IL-12. A biological activity of IL-12 in the context of the present invention is the stimulation of NK or T cells by said IL-12 polypeptide, most prominently the stimulation of T effector cells acting through perforin.

In one embodiment of the combination medicament, said IL-12 polypeptide comprises a polypeptide sequence at least 95%, 96%, 97%, 98% or 99% identical to the sequence of human p35 (SEQ ID 05), and a polypeptide sequence at least 95%, 96%, 97%, 98% or 99% identical to the sequence of human p40 (SEQ ID 06).

In the context of the present specification, the terms sequence identity and percentage of sequence identity refer to a single quantitative parameter representing the result of a sequence comparison determined by comparing two aligned sequences position by position. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Software for performing BLAST analyses is publicly available, e.g., through the National Center for Biotechnology-Information (http://blast.ncbi.nlm.nih.gov/).

One example for comparison of amino acid sequences is the BLASTP algorithm that uses the default settings: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear. Unless stated otherwise, sequence identity values provided herein refer to the value obtained using the BLAST suite of programs (Altschul et al., J. Mol. Biol. 215:403-410 (1990)) using the above identified default parameters for protein and nucleic acid comparison, respectively. In one embodiment, said IL-12 polypeptide is a recombinant human IL-12. In one embodiment, said IL-12 polypeptide is a synthetic human IL-12. In one embodiment, said IL-12 polypeptide is a fusion peptide comprising the crystallisable fragment (Fc region) of a human immunoglobulin. According to one embodiment, the IL-12 polypeptide comprises a crystallisable fragment of human immunoglobulin G. A crystallizable fragment in the context of the present invention refers to the second and third constant domain of the IgG molecule. The fragment crystallizable region (Fc region) is the tail region of an immunoglobulin antibody that interacts with cell surface receptors (Fc receptors) and proteins of the complement system. In IgG antibody isotypes, the Fc region is composed of two identical protein fragments, derived from the second and third constant domains of the antibody's two heavy chains.

According to one embodiment, the IL-12 polypeptide comprises a crystallisable fragment of human immunoglobulin G4. According to one embodiment, the IL-12 polypeptide has or comprises the sequence of SEQ ID 01. According to another embodiment, the IL-12 polypeptide comprises a sequence at least 95%, 96%, 97%, 98% or 99% identical to the sequence of SEQ ID 01.

Embodiments wherein IL-12 polypeptide chains are fused to immunoglobulin Fc fragments show different pharmacokinetic behaviour in comparison to the recombinant cytokine, which for some applications may confer a benefit.

In one embodiment, the IL-12 polypeptide component of the combination medicament is provided as a dosage form for local (intratumoural) administration or delivery. Such dosage form for local (intratumoural) administration may be a slow-release form or depot form, from which said IL-12 polypeptide is released over a number of hours to weeks. In one embodiment, the IL-12 polypeptide component of the combination medicament is administered via convection enhanced delivery (CED) or a variation thereof, for example the device shown in US2011137289 (A1) (incorporated herein by reference).

Figure 11:
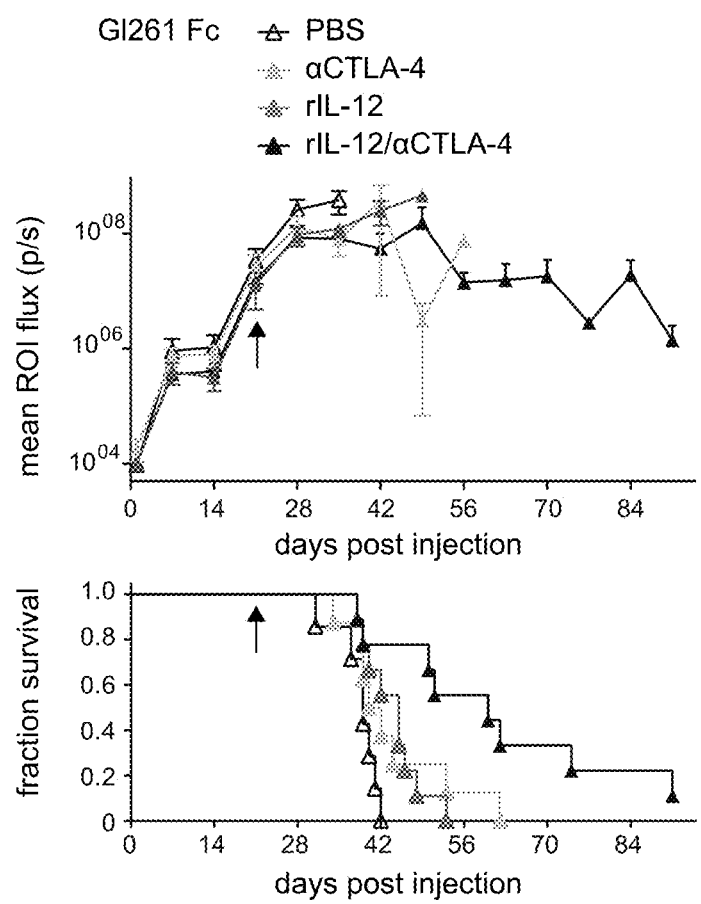
FIG. 11 shows systemic administration of recombinant heterodimeric IL-12 in combination with CTLA4 blockade $2\times10^4$ G1261 Fc cells were injected into the right striatum of wt mice and tumor growth was followed for 90 days.

In one embodiment, the IL-12 polypeptide is administered systemically together with systemic CTLA-4/PD-1/PD-L1/PD-L2 blockade. Heterodimeric recombinant IL-12 (peprotech) applied systemically together with systemic CTLA-4 blockade (i.p.) achieved a significant improvement in survival in comparison to either agent administered by itself (see FIG. 11).

In another embodiment, the IL-12 polypeptide is administered systemically together with systemic LAG-3, TIM-3, BLTA, TIGIT, VISTA or B7/H3 blockade.

In the context of the present invention, a non-agonist CTLA-4 ligand is a molecule that binds selectively to CTLA-4 under conditions prevailing in peripheral blood, without triggering the biological effect of CTLA-4 interaction with any of the physiological ligands of CTLA-4, particularly CD80 and/or CD86.

In the context of the present invention, a non-agonist PD-1 ligand is a molecule that binds selectively to PD-1 under conditions prevailing in peripheral blood, without triggering the biological effect of PD-1 interaction with any of the physiological ligands of PD-1, particularly PD-L1 or PD-L2. A non-agonist PD-L1 (PD-L2) ligand is a molecule that binds selectively to to PD-L1 (or to PD-L2) under conditions prevailing in peripheral blood, without triggering the biological effect of PD-L1 (PD-L2) interaction with any of its physiological ligands, particularly PD-1.

Similarly, in the context of the present invention, a non-agonist LAG-3, TIM-3, BLTA, TIGIT, VISTA or B7/H3 ligand, such as a polypeptide ligand, is a molecule that binds selectively to LAG-3, TIM-3, BLTA, TIGIT, VISTA or B7/H3 under conditions prevailing in peripheral blood, without triggering the biological effect of LAG-3, TIM-3, BLTA, TIGIT, VISTA or B7/H3 with any of the physiological ligands of LAG-3, TIM-3, BLTA, TIGIT, VISTA or B7/H3.

In some embodiments, said non-agonist CTLA-4 ligand is a polypeptide binding to CTLA-4. In some embodiments, said non-agonist PD-1 ligand is a polypeptide binding to PD-1.

A non-agonist CTLA-4 ligand in the sense of the invention refers to a molecule that is capable of binding to CTLA-4 with a dissociation constant of at least $10^{-7}$ $M^{-1}$, $10^{-8}$ $M^{-1}$ or $10^{-9}$ $M^{-1}$ and which inhibits the biological activity of its respective target. A a non-agonist PD-1 ligand or a non-agonist PD-L1 (PD-L2) ligand in the sense of the invention refers to a molecule that is capable of binding to PD-L1 (PD-L1, PD-L2) with a dissociation constant of at least $10^{-7}$ $M^{-1}$, $M^{-8}$ $M^{-1}$ or $10^{-9}$ $M^{-1}$ and which inhibits the biological activity of its respective target.

A non-agonist polypeptide ligand may be an antibody, an antibody fragment, an antibody-like molecule or an oligopeptide, any of which binds to and thereby inhibits CTLA-4, PD-1 PD-L1 (PD-L2), LAG-3, TIM-3, BLTA, TIGIT, VISTA or B7/H3 respectively.

An antibody fragment may be a Fab domain or an Fv domain of an antibody, or a single-chain antibody fragment, which is a fusion protein consisting of the variable regions of light and heavy chains of an antibody connected by a peptide linker. The inhibitor may also be a single domain antibody, consisting of an isolated variable domain from a heavy or light chain. Additionally, an antibody may also be a heavy-chain antibody consisting of only heavy chains such as antibodies found in camelids. An antibody-like molecule may be a repeat protein, such as a designed ankyrin repeat protein (Molecular Partners, Zurich).

An oligopeptide according to the above aspect of the invention may be a peptide derived from the recognition site of a physiological ligand of CTLA-4, PD-1 or PD-L1 or PD-L2. Such oligopeptide ligand competes with the physiological ligand for binding to CTLA-4, PD-1 or PD-L1 or PD-L2, respectively.

An oligopeptide according to the above aspect of the invention may be a peptide derived from the recognition site of a physiological ligand of LAG-3, TIM-3, BLTA, TIGIT, VISTA or B7/H3. Such oligopeptide ligand competes with the physiological ligand for binding to LAG-3, TIM-3, BLTA, TIGIT, VISTA or B7/H3. Particularly, a non-agonist CTLA-4 ligand or non-agonist PD-1 ligand or non-agonist PD-L1 ligand or non-agonist PD-L2 ligand does not lead to attenuated T cell activity when binding to CTLA-4, PD-1, PD-L1 or PD-L2, respectively, on the surface on a T-cell. In certain embodiments, the term "non-agonist CTLA-4 ligand" or "non-agonist PD-1 ligand" covers both antagonists of CTLA-4 or PD-1 and ligands that are neutral vis-à-vis CTLA-4 or PD-1 signalling. In some embodiments, non-agonist CTLA-4 ligands used in the present invention are able, when bound to CTLA-4, to sterically block interaction of CTLA-4 with its binding partners CD80 and/or CD86 and non-agonist PD-1 ligands used in the present invention are able, when bound to PD-1, to sterically block interaction of PD-1 with its binding partners PD-L1 and/or PD-L2.

In one embodiment, said non-agonist CTLA-4 ligand is a gamma immunoglobulin binding to CTLA-4, without triggering the physiological response of CTLA-4 interaction with its binding partners CD80 and/or CD86.

In some embodiments, said non-agonist PD-1 ligand is a gamma immunoglobulin binding to PD-1, without triggering the physiological response of PD-1 interaction with its binding partners PD-L1 and/or PD-L2.

In some embodiments, said non-agonist PD-L1 (PD-L2) ligand is a gamma immunoglobulin binding to PD-L1 (PD-L2), without triggering the physiological response of PD-1 interaction with its binding partners PD-L1 and/or PD-L2.

Non-limiting examples for a CTLA-4 ligand are the clinically approved antibodies tremelimumab (CAS 745013-59-6) and ipilimumab (CAS No. 477202-00-9; Yervoy).

Non-limiting examples for a PD-1/PD-L1 or PD-L2 ligands are the antibodies MDX-1105/BMS-936559, MDX-1106/BMS-936558/ONO-4538, MK-3475/SCH 900475 or AMP-224 currently undergoing clinical development The term "gamma immunoglobulin" in this context is intended to encompass both complete immunoglobulin molecules and functional fragments thereof, wherein the function is binding to CTLA-4, PD-1 or PD-L1 (PD-L2) as laid out above.

In one embodiment, the combination therapy comprises two distinct dosage forms, wherein said IL-12 polypeptide is provided as a dosage form for intratumoural delivery or local delivery in the vicinity of the tumour, and said non-agonist CTLA-4 ligand or non-agonist PD-1 ligand is provided as a dosage form for systemic delivery, particularly by intravenous injection. However, said non-agonist CTLA-4 ligand or non-agonist PD-1 ligand may also be locally applied in the same way as the IL-12 polypeptide. According to another embodiment, the IL-12 polypeptide is applied directly to the tumour draining lymph node.

According to another embodiment, the combination therapy comprises a dosage form whereby said IL-12 polypeptide is provided for intracranial delivery, e.g. by injection.

According to another aspect of the invention, a combination medicament is provided as set forth above, for use in a method of therapy of a malignant neoplastic disease, particularly solid cancerous lesions. In one embodiment, the malignant neoplastic disease is glioma. In one embodiment, the malignant neoplastic disease is a secondary brain tumour (brain metastasis of a neoplastic lesion arising outside the brain). In one embodiment, the disease is glioblastoma multiforme. In one embodiment, the malignant neoplastic disease is meningioma. In one embodiment, the malignant neoplastic disease is melanoma. In one embodiment, the malignant neoplastic disease is pancreatic cancer. In one embodiment, the malignant neoplastic disease is lung cancer. In one embodiment, the malignant neoplastic disease is prostate cancer. In one embodiment, the malignant neoplastic disease is bladder cancer.

Cancerous lesions have the propensity to spread into neighbouring tissue as well as distinct locations in the body, depending on their origin. 20-40% of all cancers develop brain metastasis; among those lung, breast and skin (melanoma) cancer are the most common sources of brain metastases (Sofietti et al., *J Neurol* 249, 1357-1369 (2002)). Similar to primary malignant brain tumours, brain metastases have a poor prognosis despite treatment and are quickly fatal. T-cells are the crucial effector cell population for IL-12 mediated tumor rejection in the brain. IL-12 together with anti-CTLA-4, anti-PD-1, anti-PD-L1 or anti-PD-L2 combination treatment addresses especially the T-cells to activate and repolarize them.

Since brain metastases grow in the same immune-compartment as primary brain tumors, patients suffering from secondary brain tumors also benefit from the combination treatment.

In one embodiment, the combination medicament comprises an IL-12 polypeptide having a biological activity of IL-12 provided as a fusion protein comprising the amino acid of human p40, the amino acid sequence of human p35 and the crystallisable fragment of human IgG4, said IL-12 polypeptide being formulated as a dosage form for intratumoural delivery. According to this embodiment, the combination medicament further comprises an immunoglobulin G raised against CTLA-4 or PD-1 as a non-agonist CTLA-4 ligand and/or a non-agonist PD-1 ligand formulated as a dosage form for systemic delivery. According to this embodiment, the combination medicament is provided for the treatment of malignant neoplastic disease, particularly for glioma, glioblastoma multiforme, meningioma, melanoma, pancreatic cancer, breast cancer, lung cancer, prostate cancer or bladder cancer.

According to yet another aspect of the invention, an IL-12 polypeptide having a biological activity of IL-12, and a non-agonist CTLA-4 ligand and/or non-agonist PD-1 ligand are used in the manufacture of a combination medicament for use in a method of therapy of a malignant neoplastic disease, particularly of glioma and other solid tissue tumours, such as glioblastoma multiforme, meningioma, melanoma, pancreatic cancer, breast cancer, lung cancer, prostate cancer or bladder cancer.

According to yet another aspect of the invention, a method is provided for treating a patient suffering from malignant neoplastic disease, particularly glioma and other solid tissue tumours, comprising the administration of an IL-12 polypeptide having a biological activity of IL-12, and a non-agonist CTLA-4 ligand and/or a non-agonist PD-1 ligand to said patient.

According to an alternative aspect of the invention, a combination therapy comprises an IL-12 nucleic acid expression vector encoding an encoded IL-12 polypeptide having a biological activity of IL-12, and a T cell inhibition blocker agent selected from
  a non-agonist CTLA-4 ligand and
  a non-agonist PD-1 or PD-L1 or PD-L2 ligand.

Figure 1B:
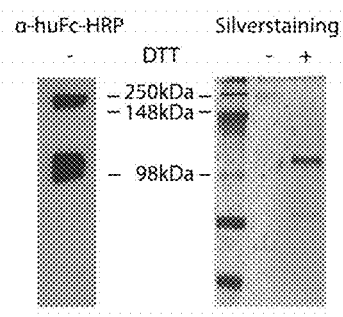
FIG. 1b shows the fusion protein given SEQ ID 01, left picture shows an immunoblot using reducing conditions, developed with an HRP-coupled polyclonal anti-human Fc antibody, right picture shows a silver staining of the fusion protein under non-reducing (DTT−) and reducing conditions (DTT+)
Figure 1C:
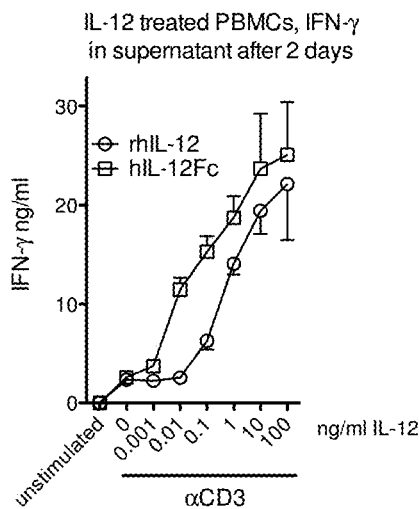
FIG. 1c shows IFN-γ production in human peripheral blood monocytic cells (PBMCs) as assessed by enzyme linked immunosorbent assay (ELISA). Cells were stimulated either with commercially available heterodimeric recombinant human IL-12 (rhIL-12) or with the purified fusion protein given SEQ ID 01 (hIL-12Fc) in the presence of an antibody directed against CD3 (polyclonal T-cell stimulation). Unstimulated: neither IL-12 stimulation nor anti-CD3 stimulation (baseline control). Experiment was performed in triplicates, error bars denote s.e.m. data representative of three independent experiments

The CTLA-4 ligand and a non-agonist PD-1 ligand may be embodied by polypeptides, particularly by antibodies, as set forth above. One non-limiting example for an encoded IL-12 polypeptide is a crystallisable immunoglobulin G fragment fused to the IL-12 constituent polypeptide chains, human IL-12 or a functional equivalent thereof. One non-limiting example is a fusion construct having the constituent polypeptides of IL-12 linked by a short amino acid sequence as depicted in FIG. 1, the amino acid sequence for which is given as SEQ ID 01 and the encoding nucleic acid sequence is given as SEQ ID 07.

According to yet another aspect of the invention, a polypeptide peptide is provided comprising
  a. a polypeptide sequence at least 95% identical to the sequence of human p35 (SEQ ID 05), and
  b. a polypeptide sequence at least 95% identical to the sequence of human p40 (SEQ ID 06) and
  c. a human immunoglobulin G subgroup 4 crystallisable fragment.

In some embodiments, the polypeptide comprises or essentially consists of a sequence at least 95%, 96%, 97%, 98%, 99% identical to SEQ ID 01, or is SEQ ID 01.

The advantage of using fusion proteins cytokines and the crystallisable fragment of immunoglobulins rather than the recombinant cytokine is improved pharmacokinetics (Belladonna et al. *J Immunol* 168, 5448-5454 (2002); Schmidt, *Curr Opin Drug Discov Devel* 12, 284-295 (2009); Eisenring et al., *Nat Immunol* 11, 1030-1038 (2010)).

The IL-12 nucleic acid expression vector according to this aspect of the invention may, by way of non-limiting example, be a "naked" DNA expression plasmid comprising a nucleic acid sequence encoding the IL-12 polypeptide under control of a promoter sequence operable in a human tumour cell, for delivery into the tumour, for example by intracranial injection. The IL-12 nucleic acid expression vector may similarly be a viral vector, for example an adeno-associated virus, an adenovirus, a lentivirus or a herpes virus.

Such IL-12 nucleic acid expression vector may be provided as a dosage form for intratumoural delivery in combination with a protein non-agonist CTLA-4 ligand and/or a non-agonist PD-1 ligand as set forth above. Similarly, the scope of the present invention encompasses the use of such IL-12 nucleic acid expression vector, in combination with a non-agonist CTLA-4 ligand and/or a non-agonist PD-1 ligand, in a method of making a combination medicament for use in therapy of malignant neoplastic disease, particularly glioma, glioblastoma multiforme, meningioma, melanoma, pancreatic cancer, lung cancer, prostate cancer or bladder cancer. Likewise, a method is provided for treating a patient suffering from malignant neoplastic disease, particularly glioma or other solid tissue tumours, comprising the administration of an IL-12 nucleic acid expression vector having a biological activity of IL-12, and a non-agonist CTLA-4 ligand and/or a non-agonist PD-1 ligand to said patient.

EXAMPLES

Example 1

Methods

Animals

C57BL/6 mice were obtained from Janvier; $b2m^{-/-}$, $Ia(b)^{-/-}$, $Il12rb2^{-/-}$, $Rag1^{-/-}$, $Rag2^{-/-}Il2rg^{-/-}$, $Prf1^{-/-}$ and $Ifng^{-/-}$ mice were obtained from Jackson Laboratories. $Il15ra^{-/-}$ mice were provided by S. Bulfone-Paus. All animals were kept in house under specific pathogen-free conditions at a 12 hour light/dark cycle with food and water provided ad libitum. All animal experiments were approved by the Swiss Cantonary veterinary office (16/2009).

Mouse Tumour Cell Lines

C57/B16 murine glioma (G1261) cells (kindly provided by A. Fontana, Experimental Immunology, University of Zurich) were transfected with pG13-ctrl (Promega) and pGK-Puro (kindly provided by T. Buch, Technical University Munich). Linearized constructs were electroporated in a 10:1 ratio using an eppendorf multiporator, then selected with 0.8 μg/ml puromycin (Sigma-Aldrich) to generate luciferase-stable G1261 cells. A single clone was isolated by limiting dilution and passaged in vivo by intracranial tumour inoculation, followed by tumour dissociation after 4 weeks and re-selection in 0.8 μg/ml puromycin. Subsequently, cells were electroporated with pCEP4-mIgG3, pCEP4-mI-12mIgG3 (SEQ ID 09) and pCEP4-mII-23mIgG3 (SEQ ID 08) (Eisenring et al, 2010) and bulk-selected with 0.8 μg/ml puromycin and 0.23 mg/ml hygromycin (Sigma-Aldrich). Cytokine production was detetected by ELISA (OptEIA Il-12/23p40, BD Pharmingen) and rt-PCR (IgG3fw: ACACACAGCCTGGACGC (SEQ ID 03) IgG3rev: CATTGAACTCCTTGCCCCT (SEQ ID 04)). G1261 cells and derived cell lines were maintained in Dulbecco's modified Eagle's medium (Gibco, Invitrogen) supplemented with 10% fetal calf serum (FCS) in presence of selection antibiotics as indicated above at 37° C. and 10% $CO_2$. B16-F10 murine melanoma cells were purchased from ATCC.

Expression and Purification of IL-12Fc

IL-12Fc (SEQ ID 02) was expressed in 293T cells after calcium phosphate-mediated transfection according to standard protocols with 45 μg of vector DNA (pCEP4-mIL-12IgG3, SEQ ID 09)/15 cm tissue culture plate. Supernatant was harvested 3 days and 6 days after transfection, sterile filtered and diluted 1:1 in PBS. The protein was purified using a purifier (AktaPrime) over a protein G column (1 ml, HiTrap, GE Healthcare) eluted with 0.1 M glycine pH 2 and dialyzed over night in PBS pH 7.4. Concentration and purity of IL-12Fc (SEQ ID 02) was measured by ELISA (OptEIA Il-12/23p40, BD Pharmingen) and SDS-PAGE followed by silverstaining and immunoblotting. IL-12Fc was detected with a rat anti mouse IL-12p40 antibody (C17.8, BioExpress) and a goat anti-rat HRP coupled antibody (Jackson). The same procedure was used for the expression of human IL-12Fc (SEQ ID 01, 07).

Characterization of Human IL-12Fc

Concentration and purity of human IL-12Fc (SEQ ID 01) was measured by ELISA (Human IL-12 (p70), Mabtech, #2455-1H-6) and SDS-PAGE followed by silver staining and immunoblotting. The human IgG4 tag was detected with an HRP-coupled goat anti human IgG antibody (#A0170, Sigma). For functional characterization of human IL-12Fc (SEQ ID 01) PBMCs, acquired according to the ethical guidelines of the University of Zurich, were plated at 100'000 cells per well in RPMI medium supplemented with 10% fetal calf serum (FCS) in 96 well plates and stimulated with either recombinant human IL-12 (Peprotech) or human IL-12Fc (SEQ ID 01). Both cytokines were normalized to each other according to concentrations derived from human IL-12p70 ELISA (Mabtech, #2455-1H-6). PBMCs were stimulated in the presence of 1 µg/ml of a mouse IgG2a anti-human CD3 antibody (OKT3, Bio-X-cell). After two days of culture in 5% $CO_2$ and 37° C., supernatant was harvested and subjected to an anti-human IFN-γ ELISA (Mabtech, #3420-1H-6).

Orthotopic Glioma Inoculation

Briefly, 6-10 week old mice were i.p. injected with Fluniximin (Biokema, 5 mg/kg body weight) before being anaesthesized with 3-5% isoflurane (Minrad) in an induction chamber. Their heads were shaved with an electric hair-trimmer. After being mounted onto a stereotactic frame (David Kopf Instruments), the animals' scalp was disinfected with 10% iodine solution and a skin incision was made along the midline. Anaesthesia on the stereotactic frame was maintained at 3% isoflurane delivered through a nose adaptor (David Kopf Instruments). Subsequently, a blunt ended syringe (Hamilton, 75N, 26s/2"/2, 5 µl) was mounted on a microinjection pump on the manipulator arm and placed 1.5 mm lateral and 1 mm frontal of bregma. The needle was lowered into the manually drilled burr hole at a depth of 4 mm below the dura surface and retracted 1 mm to form a small reservoir. Using the microinjection pump (UMP-3, World Precision Instruments Inc.) $2 \times 10^4$ cells were injected in a volume of 2 µl at 1 µl/min. After leaving the needle in place for 2 min, it was retracted at 1 mm/min. The burr hole was closed with bone wax (Aesculap, Braun) and the scalp wound was sealed with tissue glue (Indermil, Henkel).

In Vivo Bioluminescent Imaging

Tumour bearing mice were carefully weighed, anaesthesized with isoflurane (2-3%) and injected with D-Luciferin (150 mg/kg body weight, CaliperLifesciences). Animals were transferred to the dark chamber of a Xenogen IVIS 100 (CaliperLifesciences) imaging system, anaesthesia was maintained at 2% isoflurane via nosecones. 10 min after injection luminescence was recorded. Data was subsequently analyzed using Living Image 2.5 software (Caliper-Lifesciences). A circular region of interest (ROI; 1.46 cm Ø) was defined around the animals' head and photon flux of this region was read out and plotted.

Treatment of Established Gliomas

At d21 after implantation of the glioma cells, the tumour bearing animals were evenly distributed among experimental groups based on their ROI-photon flux. Animals with an ROI flux of less than $1 \times 10^5$ p/s were considered as non-takers and excluded. 40-48 h prior to implantation (2 days before beginning of treatment), osmotic pumps (Model 2004, 0.25 µl/h; Alzet) were filled with murine IL-12Fc (SEQ ID 02, 8.33 ng/µl in PBS) or PBS alone and primed at 37° C. in PBS. Immediately prior to surgery, mice were injected with Fluniximin i.p. (Biokema, 5 mg/kg body weight). Mice were anaesthesized with 3-5% isoflurane, the scalp was disinfected and a midline incision was made. The previous burr hole of the glioma injection was located, the bone wax and periost removed and the pump placed into a skin pouch formed at the animal's back. The infusion cannula was lowered through the burr hole 3 mm into the putative center of the tumour. The cannula was connected to the pump (brain infusion kit III 1-3 mm, Alzet) via a silicon tube and held in place with cyanoacrylate adhesive. The skin was sutured with a 4-0 nylon thread. Following surgery, mice were treated for 3 days with 0.1% (v/v) Borgal (Intervet) in the drinking water. Pumps were explanted at day 49. Five doses of anti mouse-CTLA-4 mouse-IgG2b antibodies (clone 9D9, bio-X-cell; Peggs et al.; *J Exp Med* 206, 1717-1725 (2009)) or an equivalent volume of PBS were i.p. injected at days 22 (200 µg), 26 (100 µg), 29 (100 µg), 35 (100 µg) and 42 (100 µg).

Figure 9:
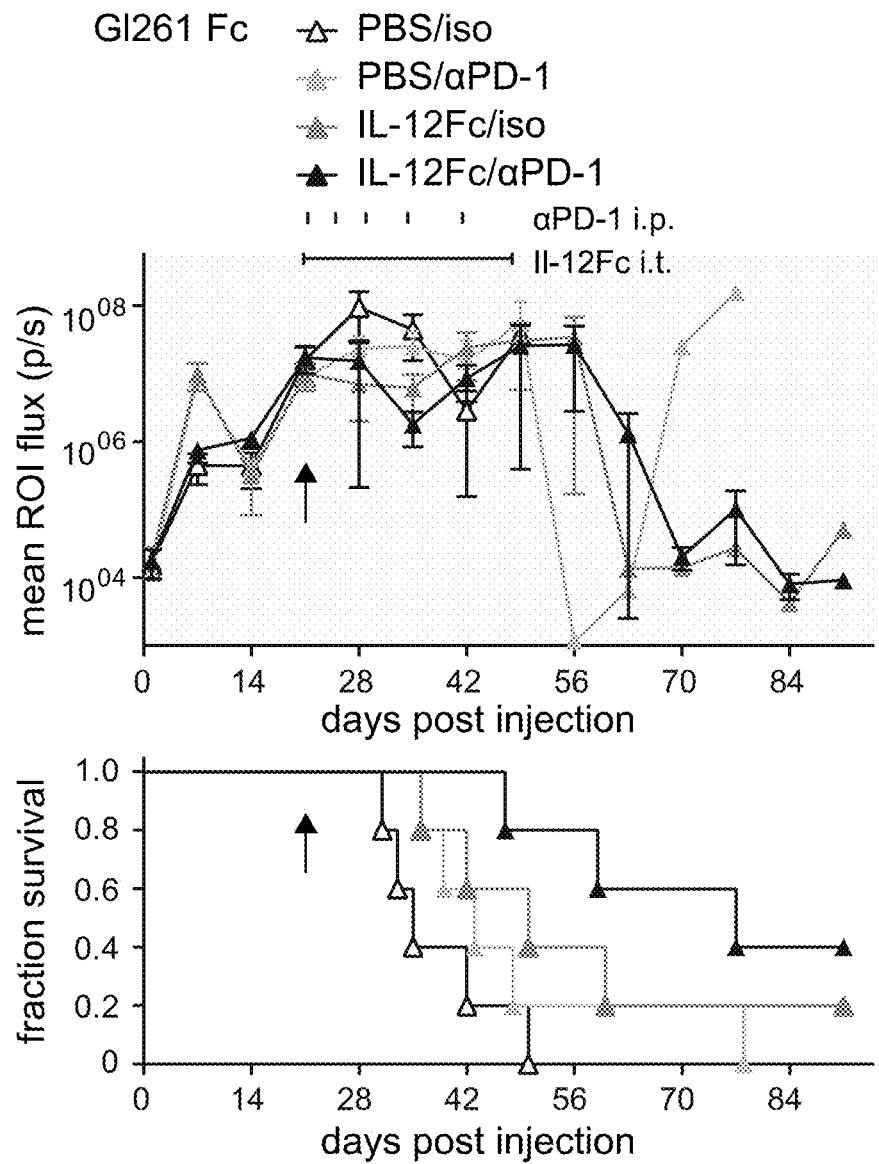
FIG. 9 shows tumour growth in wt mice inoculated with $2\times10^4$ G1261 Fc cells. Treatment started at day 21 (arrows). Osmotic minipumps delivering IL-12Fc (SEQ ID 02) into the tumour were implanted into glioma bearing animals. Animals received i.p. injections of αPD-1 blocking antibodies or isotype control antibodies starting at day 22, followed by injections as indicated in figure. Upper graph: quantification of ROI photon flux of tumour bearing wt animals receiving the indicated treatment. Lower graph: Kaplan-Meier survival analysis of the animals above; PBS/isotype vs IL-12Fc/αPD-1 p=0.0064, Log-rank (Mantel-Cox) Test. Data representative of one experiment with 5-6 animals per group.

Alternatively, animals received anti-mouse-PD-1 rat IgG2a (clone RMP1-14, bio-X-cell) or rat IgG2a isotype control antibodies (clone 2A3, bio-X-cell) for the experiment depicted in FIG. 9. Dosing schedule and application route was identical with the experiment depicted in FIG. 7. For treatment of established B16-F10 derived brain tumours, pumps were implanted at day 5 post injection, anti mouse-CTLA-4 mouse-IgG2b antibodies (clone 9D9, bio-X-cell; Peggs et al.; *J Exp Med* 206, 1717-1725 (2009)) or an equivalent volume of PBS were i.p. injected at days 6 (200 µg), 11 (100 µg), 13 (100 µg) and 19 (100 µg).

Survival Analysis of Tumour Bearing Animals

Tumour bearing animals were monitored by BLI, checked for neurological symptoms and weighed weekly until day 21 post glioma inoculation. G1261 Fc animals exhibiting an ROI flux of less than $1 \times 10^5$ p/s at day 21 were considered as non or slow-tumour takers and excluded from the survival analysis (5-10%). From day 21 onwards animals were checked daily. Animals that showed symptoms as apathy, severe hunchback posture and/or weight loss of over 20% of peak weight were euthanized. B16-F10 tumour bearing mice were scored daily starting at day 5 until the end of experiment according to the same scheme.

Histology

For histology, animals were euthanized with $CO_2$, transcardially perfused with ice-cold PBS and decapitated. Whole brains were carefully isolated, fixed in 4% Formalin, embedded in Paraffin and 3 µm sections were processed for HE staining and/or immunohistochemistry to detect F4/80 (BM8; BMA biomedicals). Primary antibodies were detected with HorseRadish Peroxidase-coupled secondary antibodies. Staining was visualized with 3,3'-Diaminobenzidin (DAB) as the HRP substrate. Pictures were generated using an Olympus BX41 light microscope equipped with an Olympus ColorViewIIIu camera and Olympus cell^B image acquisition software. Overviews of whole brains slices were cropped using Adobe Photoshop CS3.

Statistical Analysis

For statistical analysis of Kaplan-Meier survival curves, a Log-rank (Mantel-Cox) Test was used to calculate the p-values indicated in respective figures. P values of less than 0.05 were considered statistically significant. Analysis was performed with GraphPad Prism version 5.0a for Mac OSX (GraphPad Software Inc).

Example 2

Intratumoural Expression of IL-12Fc Promotes Clearance of Experimental Gliomas

We have designed and cloned a fusion protein consisting of the p40 subunit of human IL-12 linked via a flexible peptide linker to the p35 subunit. This single chain construct was then fused to the constant region of human IgG4 heavy chain (FIG. 1A). We termed this human single chain fusion protein IL-12Fc (SEQ ID 01.) We expressed this protein in HEK293 human embryonic kidney cells and detected a dimeric as well as a monomeric form under native conditions. Under reducing conditions only the monomeric form is detectable (FIG. 1B). IL-12Fc (SEQ ID 01) has similar functional properties as commercially available heterodimeric IL-12 (purchased from Peprotech). To determine if IL-12Fc (SEQ ID 01) could be suitable to overcome the local immunosuppressive environment induced by gliomas and to shed light on the effector mechanisms involved, we expressed a murine version (Belladonna et al. *J. Immunol* 168, 5448-5454 (2002), IL-12Fc (SEQ ID 02)) of this cytokine in G1261 mouse glioma cells. To measure intracranial tumour growth non-invasively via bioluminescence imaging (BLI) we first generated a G1261 line that constitutively expresses *photinus pyralis* luciferase. We termed this cell line G1261-luc. We next modified this cell line to continuously release a fusion protein of IL-12 and the crystallizable fragment of mouse immunoglobulin G3 (IL-12Fc; SEQ ID 02, 09) or Fc (SEQ ID 08) alone as a control (termed 'G1261 IL-12Fc' and 'G1261 Fc', respectively). The chosen murine protein sequence of the fusion construct is homologous to the human variant (SEQ ID 01) and consists of the subunits p40 and p35 of IL-12 which are connected by a linker (G4S)$_3$ and the subunits CH2, CH3 and the last six amino acids of CH1 of the crystallizable fragment of IgG3, whereas CH1 and CH2 are connected by a hinge region. Vectors for expression of the control fragment and the IL-12 fusion construct are depicted in SEQ ID 08 and 09, respectively. The intention of using fusion proteins rather than the recombinant cytokine was to see whether they would exhibit improved pharmacokinetics. We confirmed secretion of IL-12Fc (SEQ ID 02) by ELISA for the subunits p40 and p70. We further confirmed expression of the Fc tail by RT-PCR. When implanted intracranially into the right striatum, luminescence readings and tumour volume as assessed by stereologic methods showed a robust correlation (data not shown).

Figure 2:
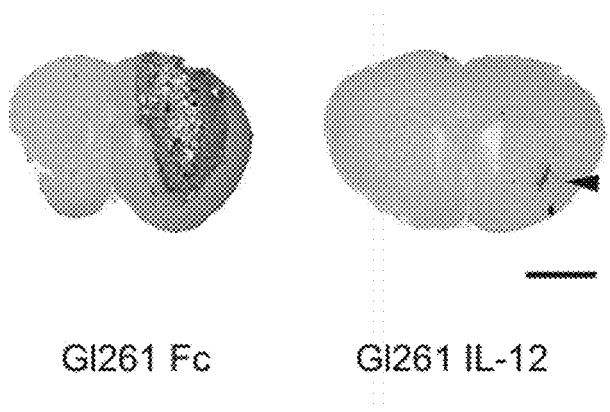
FIG. 2 shows immunohistochemistry of formalin fixed tumour sections obtained from syngeneic C57/B16 mice 5 weeks after challenge with $2\times10^4$ G1261 Fc or G1261 Fc cells and stained with antibody against F4/80, counterstain hematoxylin (representative examples, n=6 mice per group). Scale bar indicates 2 mm, arrowhead indicates residual G1261 IL-12Fc (SEQ ID 02) tumour.
Figure 3:
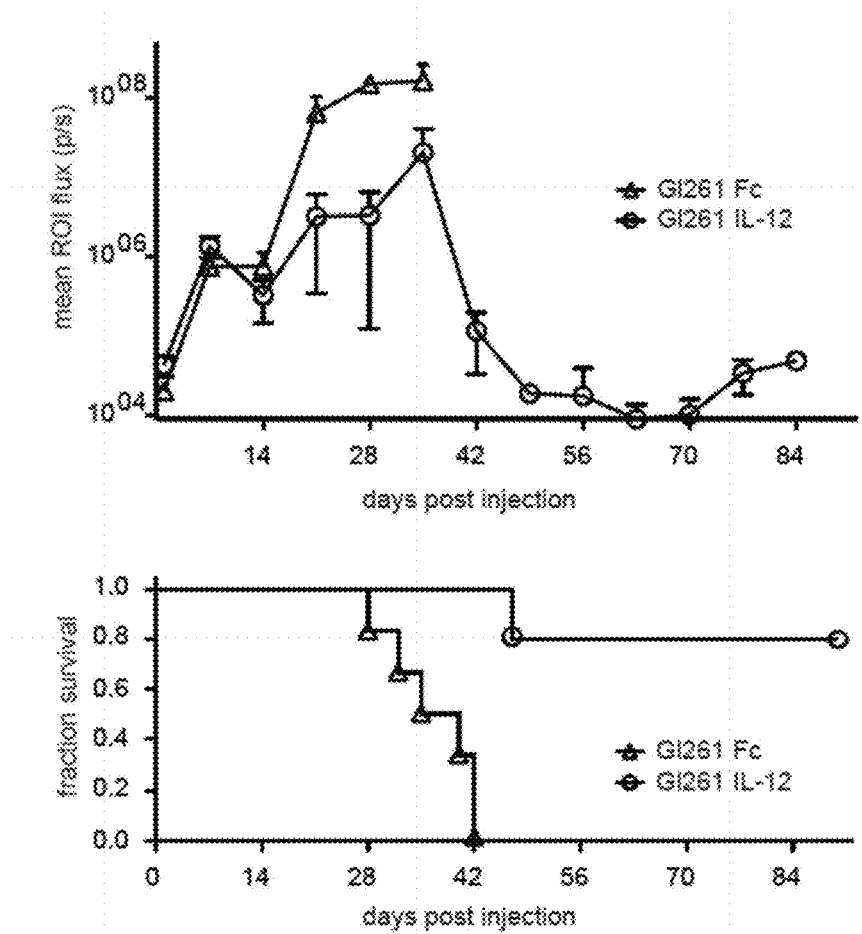
FIG. 3 shows non-invasive Bioluminescence imaging (BLI) of mouse glioma in syngeneic C57/B16 mice (n=5-6 mice per group) after implantation of $2\times10^4$ G1261 cells constitutively expressing *photinuspyralis* luciferase and releasing a fusion protein of IL-12 and the crystallizable fragment of mouse immunoglobulin G3 (G1261 IL-12Fc, (SEQ ID 02)) or Fc alone as control (G1261 Fc). Upper panel: Quantification of tumour growth which correlates to photon flux (p/s) in the region of interest (ROI) versus the days post injection of the modified glioma cells. Lower panel: Kaplan-Meier survival analysis. Data are representative of 2 independent experiments.

We next implanted G1261 IL-12Fc and Fc into the right striatum of syngenic C57B1/6 mice and followed tumour growth via non invasive bioluminescence imaging (BLI). After an initial increase in luminescence all groups showed a depression around day 14 post injection. Animals bearing Fc-expressing tumours exhibited a steep increase in BLI and soon reached withdrawal criteria, sometimes even before day 35 post injection. In contrast, BLI-readings for animals that had been injected with IL-12Fc expressing G1261 tumours dropped to levels close to the detection limit at day 21 onwards (data not shown). In agreement with this observation, we could only detect a residual tumour in some animals in this group, while Fc control-injected animals showed robust tumour formation when analyzed histologically (FIG. 2). When we followed animals that had been implanted with G1261 IL-12Fc or G1261 Fc cells for up to 90 days, we observed rejection of the tumour in a high proportion of mice bearing IL-12Fc secreting tumours after an initial establishment (FIG. 3).

Example 3

T-cells are the Major Effector Cell Type of IL-12Fc Mediated Glioma Rejection

Figures 4A, 4B:
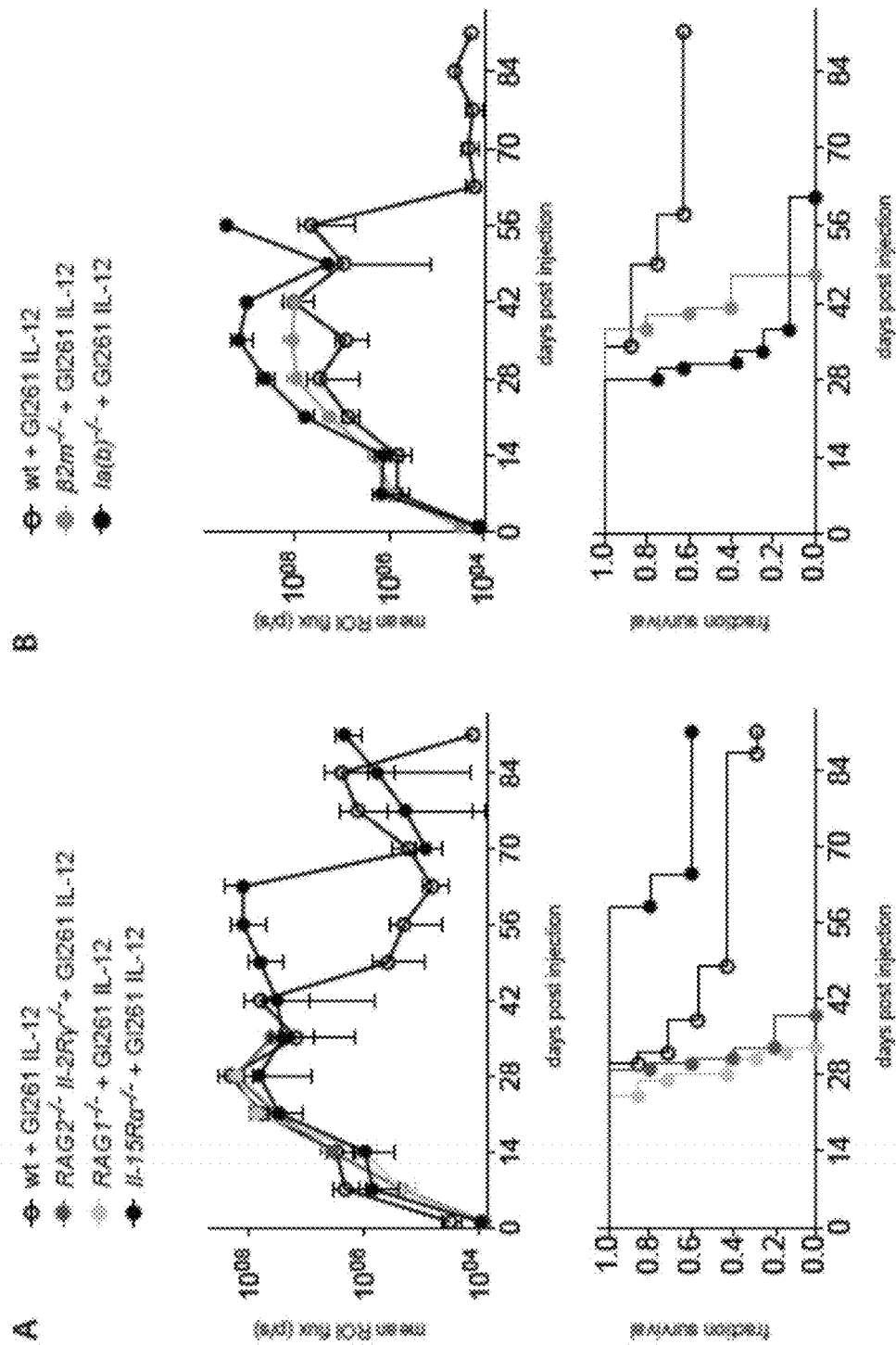
FIGS. 4A-4B show non-invasive Bioluminescence (BLI) imaging of mouse glioma in WT animals and different mouse mutants (n=5-7 mice per group) after implantation of $2\times10^4$ G1261 cells constitutively expressing *photinuspyralis* luciferase and releasing a fusion protein of IL-12 and the crystallizable fragment of mouse immunoglobulin G3 (G1261 IL-12Fc, (SEQ ID 02)). Upper panel: Quantification of tumour growth via BLI imaging versus the days post injection of the modified glioma cells. Lower panel: Kaplan-Meier survival analysis.

To confirm that the secretion of IL-12Fc by G1261 IL-12Fc acts on the host rather than the tumour cells themselves, we observed the growth of G1261 IL-12Fc and G1261 Fc to be the same in mice lacking the receptor to IL-12. The unbridled growth of G1261 IL-12 in IL-12rβ2$^{-/-}$ animals demonstrates that IL-12Fc acts specifically on a cell type in the recipient mouse (data not shown). T and NK cells are among the most prominent IL-12 responsive leukocytes. To systematically test the functional relevance of the IL-12Fc mediated influx of these cells, we challenged a series of mouse mutants with intracranial G1261 IL-12Fc. We implanted G1261 IL-12Fc cells in mice that lack T and B cells (Rag1$^{-/-}$) or conventional Nk-cells (Il-15ra$^{-/-}$) or in mice lacking both T-, B-, Nk-cells and lymphoid tissue inducer-like cells (Rag2$^{-/-}$) (FIG. 4A). After an initial lag phase until day 14 after injection, all groups exhibited a strong increase in luminescence until day 28, reflecting strong tumour growth. Between days 28 and 42 most of the animals succumbed to the tumours. Only wt and Il-15ra$^{-/-}$ mice were able to control the tumour and show a significantly prolonged survival compared to Rag2$^{-/-}$ Il2rg$^{-/-}$ and Rag1$^{-/-}$ animals. While T or B-cells appeared to be crucial for IL-12Fc mediated glioma rejection, the ability of Il-15ra$^{-/-}$ mice to reject G1261 IL-12 indicates that NK cells were largely expendable.

We next investigated the contribution of CD4- and CD8 positive T-cells using MHCII (Ia(b)$^{-/-}$) and MHCI (β2m$^{-/-}$) deficient mice. In contrast to wt mice, Ia(b)$^{-/-}$ mice lacking CD4 T cells could not control G1261 IL-12Fc tumours, and β2m$^{-/-}$ mice succumbed to the glioma shortly afterwards (FIG. 4B). The survival in both mutant groups was shortened compared to the wildtype group. These data clearly demonstrate that IL-12Fc mediated tumour rejection is dependent on the activity of T cells including helper T cells and CTLs.

Example 4

Figure 5:
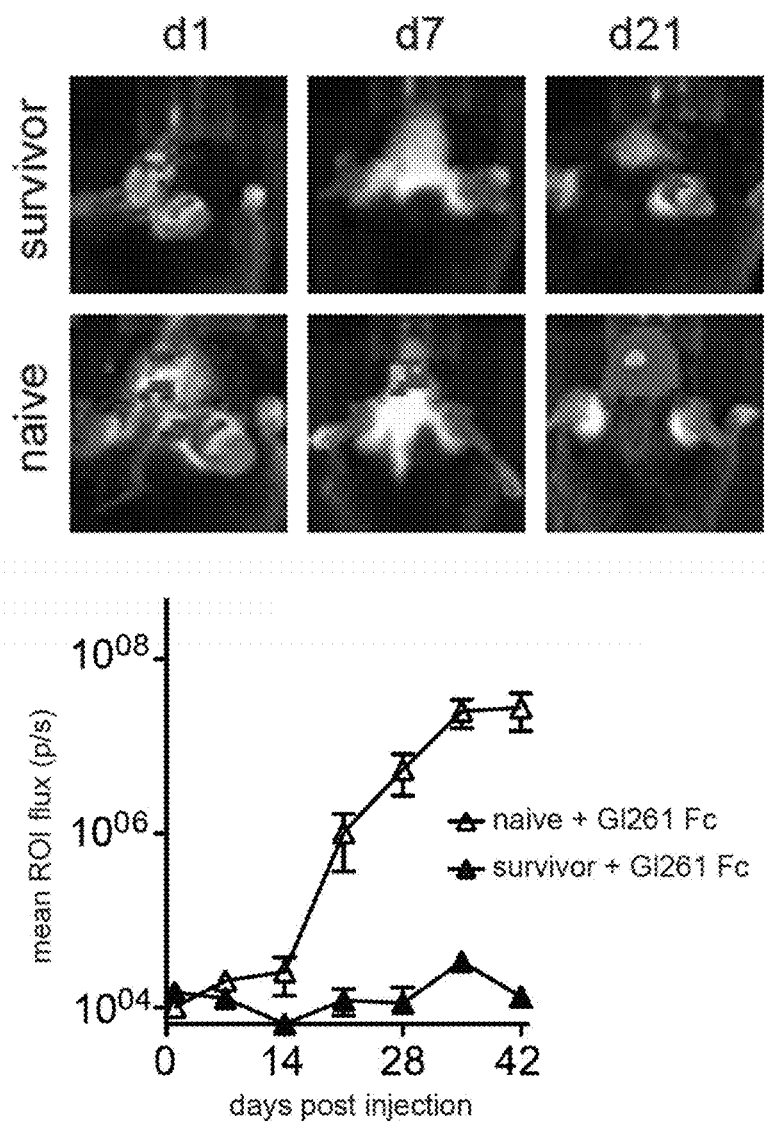
FIG. 5 shows T cell memory formation in surviving wt animals that had been previously challenged with $2\times10^4$ G1261 IL-12Fc (SEQ ID 02) cells. Examples for bioluminescence emitted from the brains of surviving wt animals that had been rechallenged with G1261 Fc cells compared to naïve wt animals is shown (upper panel, days 1, 7 and 21 post rechallenge shown). Furthermore, bioluminescence of the tumours is shown in photons per second (p/s) in the region of interest (ROI) versus the days post injection of the modified glioma cells (lower panel). A rapid rejection of the control tumours in surviving wt animals was observed. While the measured luminescence at day 1 suggested identical seeding across the two groups, only the naïve mice exhibited a measurable signal at day 7 onwards, suggesting a rapid and effectively clearing anti-glioma memory response now independent of ectopically expressed pro-inflammatory cytokines (namely IL-12Fc, (SEQ ID 02)). (n=4-6 mice/group). Data are representative of 2 independent experiments.

The Antitumoural Memory Response is Independent of Ectopically Expressed IL-12Fc To further investigate the character of the T-cell dependent tumour control, we tested the surviving wt animals that had been previously challenged with G1261 IL-12Fc cells for T cell memory formation (FIG. 5). The animals were treated as described in FIG. 3/example 1. In contrast to the primary challenge, we now injected G1261 Fc cells into the contralateral hemisphere of survivors or naïve wt animals. We observed a rapid rejection of the control tumours within days. While the measured luminescence at day 1 suggested identical seeding across the two groups, only the naïve mice exhibited a measurable signal at day 7 onwards, suggesting a rapid and effectively clearing anti-glioma memory response now independent of ectopically expressed pro-inflammatory cytokines.

Example 5

CTLs are the Main Effector Cells of IL-12Fc-mediated Glioma Rejection

Figures 6A, 6B:
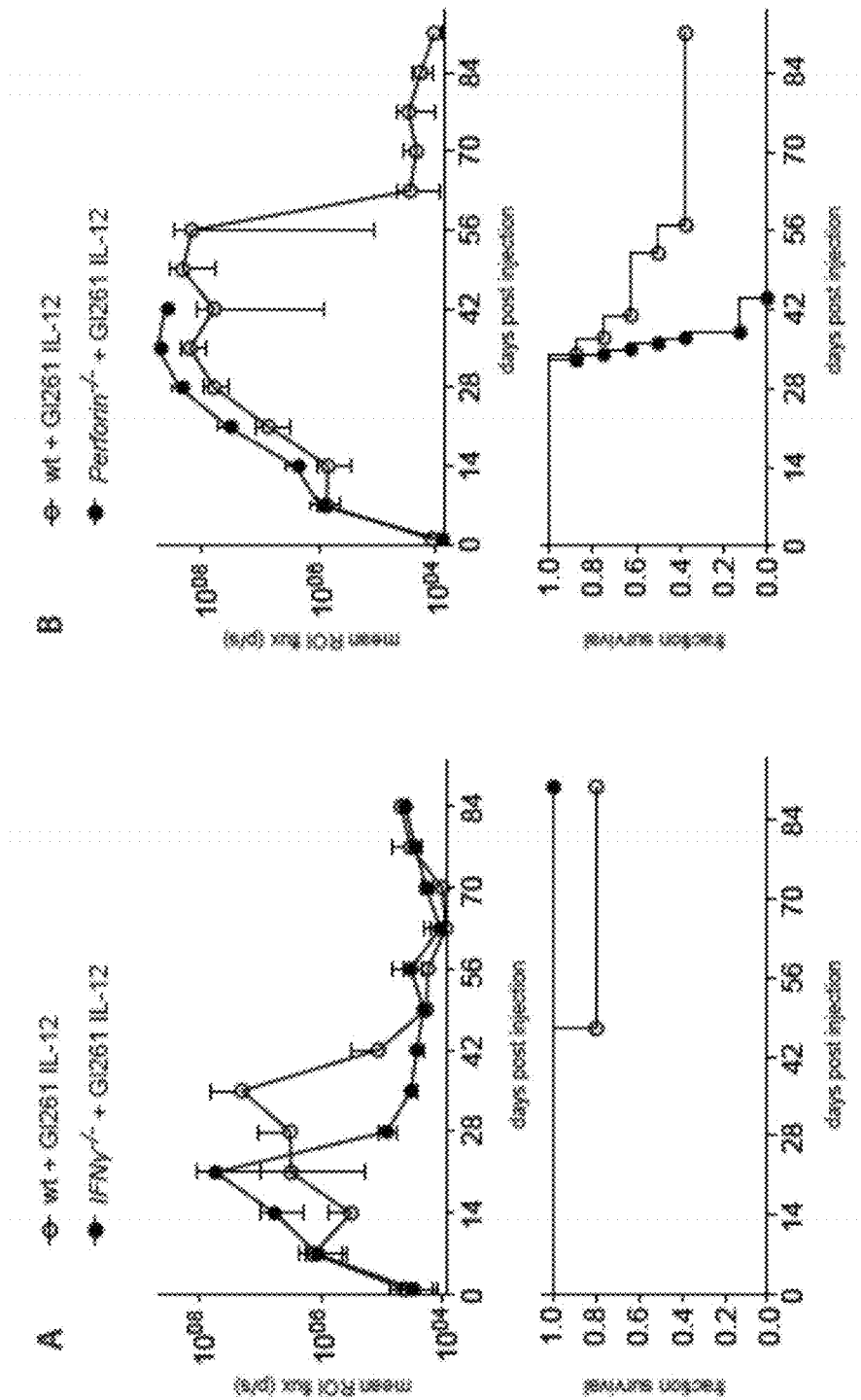
FIGS. 6A-6B show non-invasive Bioluminescence (BLI) imaging of mouse glioma in different mouse mutants (n=4-8 mice per group) after implantation of $2\times10^4$ G1261Fccells constitutively expressing *photinuspyralis* luciferase and releasing a fusion protein of IL-12 and the crystallizable fragment of mouse immunoglobulin G3 (G1261 IL-12Fc (SEQ ID 02)).

It is well established that IL-12 polarizes naive T-cells to adopt a T$_H$1 phenotype (Trinchieri, *Nat Rev Immunol* 3, 133-146 (2003)). To shed further light on the mechanistic underpinnings underlying the IL-12 induced rejection of experimental glioma, we challenged mice deficient in the T$_H$1 hallmark cytokine IFN-γ (Ifng$^{-/-}$) with IL-12Fc expressing G1261 cells (FIG. 6A). The animals were treated as described in FIG. 3/Example 1. To our surprise we observed a similar tumour rejection as in wt animals, suggesting that the mechanism of rejection is independent of IFN-γ. Conversely, IL-12 also stimulates the cytolytic activity of CTLs.

When we analyzed the role of Perforin, a cytolytic molecule primarily expressed on $CD8^+$ CTLs and Nk-cells, we observed a clear difference in survival 0 CTLs and NK cells but also $CD4^+$ T-cells. To further investigate the mechanism of IL-12Fc induced rejection of glioma, perforin-deficient mice ($prf1^{-/-}$) were challenged with IL-12Fc expressing G1261 cells. In contrast to $Ifng^{-/-}$, Perforin deficient animals ($prf1^{-/-}$) were not able to control the tumour. This further supports the notion that CTLs are the main effector cells of IL-12Fc mediated glioma rejection. A clear difference in the survival curves of wt and $prf1^{-/-}$ was observed.

Example 6

Figure 7:
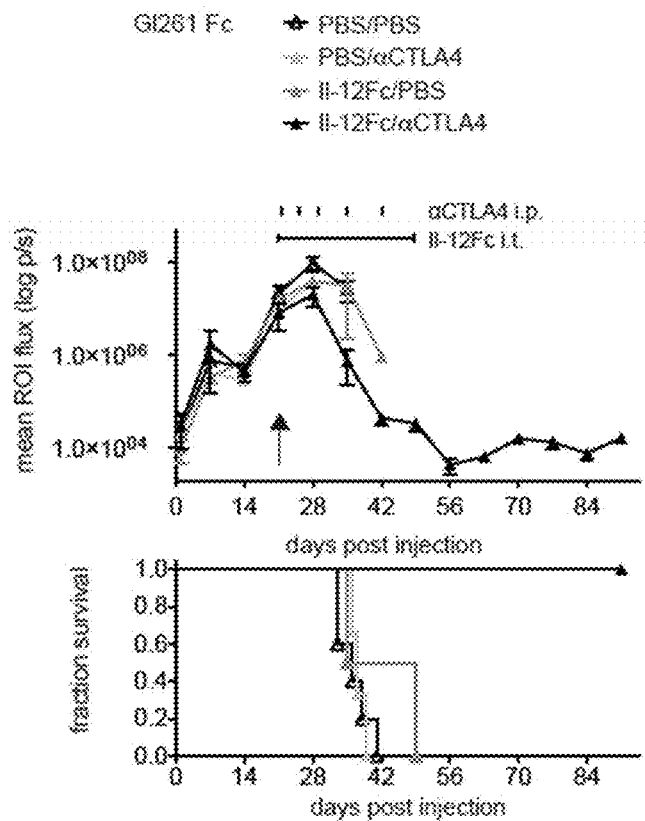
FIG. 7 shows tumour growth in wt mice inoculated with $2\times10^4$ G1261 Fc cells. Treatment started at day 21 (arrows). Osmotic minipumps delivering IL-12Fc (SEQ ID 02) (or PBS) into the tumour were implanted into glioma bearing animals. Animals received i.p. injections αCTLA-4 blocking antibodies or PBS starting at day 22, followed by injections as indicated in figure. Upper graph: quantification of ROI photon flux of tumour bearing wt animals receiving the indicated treatment. Lower graph: Kaplan-Meier survival analysis of the animals above; PBS/PBS vs IL-12Fc/αCTLA-4 p=0.0045, PBS/PBS vs IL-12Fc/PBS p=0.3435, PBS/αCTLA4 vs IL-12Fc/αCTLA-4 p=0.0101; Log-rank (Mantel-Cox) Test. Data representative of three independent experiments with 2-5 animals per group
Figure 8:
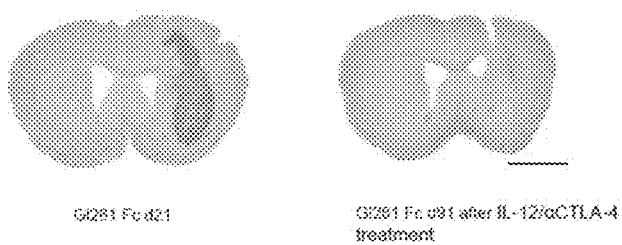
FIG. 8 shows immunohistchemistry of tumour sections obtained from syngenic C57/B16 mice after challenge with G1261 Fc cells at day 21 and after local administration of IL-12Fc (SEQ ID 02) in combination with systemic CTLA-4 blockade as described in Example 5. The sections were stained with Hematoxylin and Eosin. Scale bar indicates 2 mm.
Figure 10:
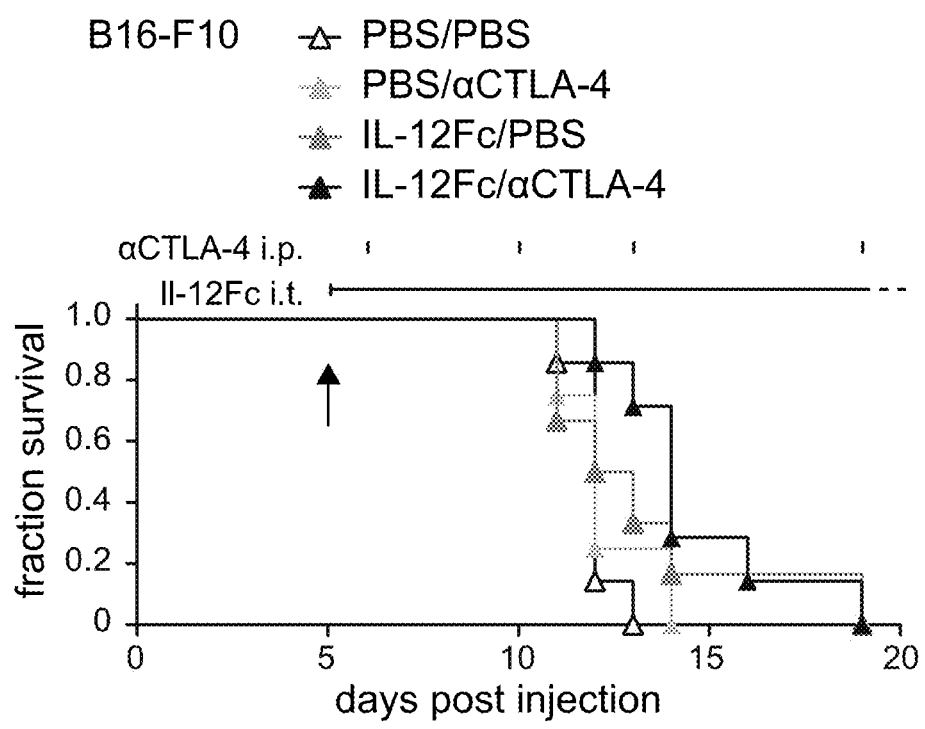
FIG. 10 shows tumour growth in wt mice in inoculated with 50 B16-F10 cells. Treatment started at day 5 (arrow). Osmotic minipumps delivering IL-12Fc (SEQ ID 02) into the tumour were implanted into glioma bearing animals. Animals received i.p. injections of αCTLA-4 blocking antibodies or PBS starting at day 6, followed by injections as indicated in figure. Kaplan-Meier survival analysis PBS/PBS vs IL-12Fc/αCTLA-4 p=0.0028, Log-rank (Mantel-Cox) Test. Data representative of one experiment with 6 animals per group.

Local Administration of IL-12Fc in Combination with Systemic CTLA-4 Blockade is Effective Against Advanced Stage Experimental Gliomas To further boost and prolong the activated phenotype of T-cells, we blocked the co-inhibitory molecule CTLA-4 via neutralizing antibodies in the next set of experiments. IL-12 was administered locally to mice with advanced stage tumours. Treatment was administered to animals that had been challenged with G1261 Fc 21 days before and that already exhibited strong bioluminescence signals, indicating an advanced stage of glioma growth. Local treatment: At day 21, osmotic minipumps delivering 50 ng IL-12Fc/day (or PBS) into the tumour were implanted into glioma bearing animals. After 28 days (day 49 after tumour injection) the empty pumps were explanted from surviving animals. Systemic treatment: At day 22, tumour bearing animals received 200 μg αCTLA-4 mouse IgG2b (9D9) or PBS i.p. Treatment was sustained with 100 μg αCTLA-4 at days 26, 29, 35 and 42 (FIG. 7). Neither IL-12Fc, nor anti-CTLA-4 alone conferred any significant survival advantage. Strikingly, the combination of local IL-12Fc administration directly into the tumour site in combination with systemic CTLA-4 blockade led to a full remission of the tumour (FIG. 8). 90 days after inoculation, histologic assessment of the brain tissue of surviving animals did not show any signs of demyelination or infiltrates. Local IL-12Fc administration in combination with systemic PD-1 blockade also led to a significant increase in surviving animals, the frequency was however lower than with systemic CTLA-4 blockade (FIG. 9). The above described combination therapy (FIG. 7) confers a significant survival advantage even in the case of intracranial growth of B16-F10 syngeneic murine melanoma cells (FIG. 10). This is not a perfect model for secondary brain tumours since it is skipping various steps of metastasis formation. Even in this more aggressive situation the combination treatment prolongs survival.

Preventive treatment of tumours in preclinical models may allow the study of immunological mechanisms and the interactions between tumour cells and tumour microenvironment. However, preventive therapy is of limited clinical relevance in the translation to treat cancer patients. We thus decided to choose an exceptionally late timepoint for intervention in a progressing and aggressive disease model. To closely mimic a clinical situation, we allowed the tumour to progress to a size that is highly likely to cause significant neurological symptoms in humans. Here, monotherapy with locally applied (intratumoural) IL-12 had a minimal albeit significant survival effect. We already observed a weak synergistic effect when we combined systemic IL-12 treatment with systemic CTLA-4 blockade. When local IL-12 infusion was combined with systemic CTLA-4 blockade, the anti-glioma effect was striking.

We claim:

1. A method of treating a patient suffering from a malignant tumor, wherein the malignant tumor is melanoma, the method comprising
   a. administering into the malignant tumor, the vicinity of the malignant tumor, or the lymph node associated with the malignant tumor, an effective amount of
      a recombinant IL-12 polypeptide comprising
      i. a human IL-12 p35 comprising the amino acid sequence SEQ ID NO:5,
      ii. a human IL-12 p40 comprising the amino acid sequence SEQ ID NO:6 and
      iii. optionally, a human immunoglobulin G crystallisable fragment; and
   b. systemically administering an effective amount of a non-agonist blockade of T-cell inhibitory antibody, wherein the antibody is an anti-PD-1 antibody, thereby treating the malignant tumor.

2. The method of claim 1, wherein the recombinant IL-12 polypeptide comprises a human immunoglobulin G subgroup 4 crystallisable fragment.

3. The method of claim 1, wherein the recombinant IL-12 polypeptide is a fusion protein comprising the human IL-12 p40 and p35 subunits and the crystallisable fragment which is of human lgG4,
   said recombinant IL-12 polypeptide is provided as a dosage form for intratumoural delivery, and wherein
   said anti-PD-1 antibody is an immunoglobulin G provided as a dosage form for systemic delivery.

4. The method of claim 1, wherein the anti-PD-1 antibody is a gamma immunoglobulin that binds to PD-1.

5. The method of claim 1, wherein the anti-PD-1 antibody is selected from the group consisting of nivolumab, pembrolizumab, and cemiplimab.

6. The method of claim 1, wherein the recombinant IL-12 polypeptide is provided as a dosage form for intratumoral injection.

7. The method of claim 1, wherein the anti-PD-1 antibody is provided as a dosage form for intravenous injection.

8. The method of claim 1, wherein the malignant tumor is a primary tumor.

9. A method of treating a patient suffering from a malignant tumor, wherein the malignant tumor is melanoma, the method comprising
   a. administering into the malignant tumor, the vicinity of the malignant tumor, or the lymph node associated with the malignant tumor, an effective amount of
      a recombinant IL-12 polypeptide comprising the amino acid sequence SEQ ID NO: 1,
   and
   b. systemically administering an effective amount of an anti-PD-1 antibody, thereby treating the malignant tumor.

* * * * *